United States Patent
Araya et al.

(10) Patent No.: US 6,479,735 B1
(45) Date of Patent: *Nov. 12, 2002

(54) TRANSGENIC PLANTS INCLUDING A TRANSGENE CONSISTING OF A HYBRID NUCLEIC ACID SEQUENCE, COMPRISING AT LEAST ONE UNEDITED MITOCHONDRIAL GENE FRAGMENT FROM HIGHER PLANTS AND PROCESS FOR PRODUCING THEM

(75) Inventors: Alejandro Araya, Talence; Armand Mouras, Pessac, both of (FR)

(73) Assignee: Centre National de la Recherche Scientifique - CNRS, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/224,997

(22) Filed: Jan. 4, 1999

Related U.S. Application Data

(62) Division of application No. 08/505,218, filed as application No. PCT/FR94/00162 on Feb. 15, 1994, now Pat. No. 5,914,447.

(30) Foreign Application Priority Data

Feb. 15, 1993 (FR) .............................................. 93 01650

(51) Int. Cl.$^7$ ......................... C12N 15/29; C12N 15/62; C12N 15/82; A01H 1/02; A01H 5/00
(52) U.S. Cl. ...................... 800/303; 800/274; 800/278; 800/286; 800/287; 800/288; 800/306; 800/309; 800/312; 800/313; 800/314; 800/316; 800/317.1; 800/317.2; 800/317.4; 800/320; 800/320.1; 800/320.2; 800/320.3; 800/322; 435/69.7; 435/69.8; 435/69.9; 435/320.1; 536/23.4
(58) Field of Search ................................. 800/274, 278, 800/286, 287, 288, 303, 306, 309, 312–314, 316, 317.1–317.2, 317.4, 320–320.3, 322; 435/69.7, 69.8, 69.9, 320.1; 536/23.4

(56) References Cited

U.S. PATENT DOCUMENTS 5,914,447 A * 6/1999 Araya et al. ................. 800/274

OTHER PUBLICATIONS

Handa et al. FEBS Letters 310(2): 111–114, Sep. 1992.*
"Novel Recombination in the Maize Mitochondrial Genome Produce a Unique Transcriptional Unit in the Texas Male–Sterile Cytoplasm," by R.E. Dewey et al., Cell, vol. 44, Feb. 14, 1986, p. 439–449.

"A Fused Mitochondrial Gene Associated with Cytoplasmic Male Sterility is Developmentally Regulated," by Ellora G. Young et al., Cell, vol. 50, Jul. 3, 1987, p. 41–49.

"The Molecular Biology and Genetic Manipulation of the Cytoplasm of Higher Plants," by David M. Lonsdale, Molecular Genetics Department, Cambridge, United Kingdom, p. 47–102.

"Induction of Male Sterility in Plants by a Chimaeric Ribonuclease Gene," by Celestina Mariani et al., Nature, vol. 347, Oct. 25, 1990, p. 737–741.

"Premature Dissolution of the Microsporocyte Callose Wall Causes Male Sterility in Transgenic Tobacco," by Dawn Worrall et al., The Plant Cell, vol. 4, Jul. 1992, p. 759–771.

"Antisense Inhibition of Flavonoid Biosynthesis in Petunia Anthers Results in Male Sterility," by Ingrid M. Van Der Meer et al., The Plant Cell, vol. 4, Mar. 1992, p. 253–262.

"One Step Generation of Cytoplasmic Male Sterility by Fusion of Mitochondrial–Inactivated Tomato Protoplasts with Nuclear–Inactivated Solanum Protoplasts," by Georg Melchers et al., Proc. Natl. Acad. Sci. USA, Aug. 1992, p. 6832–6836.

"A Yeast Mitochondrial Presequence Functions as a Signal for Targeting to Plant Mitochondria in Vivo," by Udo K. Schmitz et al., The Plant Cell, vol. 1, Aug. 1989, p. 783–791.

"Targeting of Bacterial Chloramphenicol Acetyltransferase to Mitochondria in Transgenic Plants," by Marc Boutry et al., Nature, vol. 328, Jul. 23, 1987, p. 340–342.

"Two Genes Encode the Adenine Nucleotide Translocator of Maize Mitochondria," by Brian Bathgate et al., Eur. J. Biochem, vol. 183, 1989, p. 303–310.

"Subunit IV of Yeast Cytochrome C Oxidase: Cloning and Nucleotide Sequencing of the Gene and Partial Amino Acid Sequencing of the Mature Protein," by Ammy C. Maarse et al., The EMBO Journal, vol. 3, No. 12, 1984, p. 2831–2837.

(List continued on next page.)

Primary Examiner—David T. Fox
(74) Attorney, Agent, or Firm—Lowe Hauptman Gilman & Berner, LLP

(57) ABSTRACT

Hybrid nucleic acid sequences including at least the coding region of an unedited mitochondrial gene of superior plants and controlling the male fertility of plants containing said sequences, transgenic plants having such sequences and methods of production of transgenic male-sterile plants and method of restoring male-fertile plants. The nuclei of the transgenic plants contain a hybrid sequence capable of being expressed (transgene), comprising at least one coding region of an unedited mitochondrial gene of superior plants and a sequence capable of transferring the protein expressed by said coding region, to the mitochondrion, said hybrid sequence being capable of modifying the male fertility of plants having incorporated said transgene, while leaving the other phenotype characteristics of said plants unaltered.

16 Claims, 14 Drawing Sheets

(3 of 14 Drawing Sheet(s) Filed in Color)

OTHER PUBLICATIONS

"Expression in Plants of Two Bacterial Antibiotic Resistance Genes After Protoplast Transformation with a New Plant Expression," by Maciej Pietrzak et al., *Nucleic Acids Research*, vol. 14, No. 14, 1986, p. 5857–5868.

"Callus Induction and Plant Regeneration from Mesophyll Protoplasts of *Nicotiana Sylvestris*," by J.I. Nagy et al., Institute of Plant Physiology, Hungarian Academy of Sciences, Hungary, Z. Pflanzen, 453–455.

"Streptomycin Resistant and Sensitive Somatic Hybrids of *Nicotiana Tabacum* and *Nicotiana Knightiana*: Correlation of Resistance to N. Tabacum Plastids," by L. Menczel et al., *Theor. Appl. Genet.*, 59, 1981, p. 191–195.

"Nutritional Requirements for Growth of Vicia Hajastana Cells and Protoplasts at a Very Low Population Density in Liquid Media," by K.N. Kao et al., *Planta*, 1975, p. 105–110.

"Nutritional Requirements of Protoplast–derived, Haploid Tobacco Cells Grown at Low Cell Densities in Liquid Medium," by Michel Caboche, *Planta*, 149, 1980, p. 7–18.

"Haploid Plants from Pollen Grains," by N.P. Nitsch et al., *Science*, vol. 163, Jan. 3, 1969, p. 85–87.

"Ribosomal DNA Spacer–Length Polymorphisms in Barley: Mendelian Inheritance, Chromosomal Location, and Population Dynamics," by M.A. Saghai–Maroof et al., *Proc. Natl. Acad. Sci. USA*, vol. 81., Dec. 1984, p. 8014–8018.

"Reconstitution and Molecular Analysis of the Respiratory Chain," by V.M. Darley–Usmar et al., Ch. 5, p. 113–152.

* cited by examiner

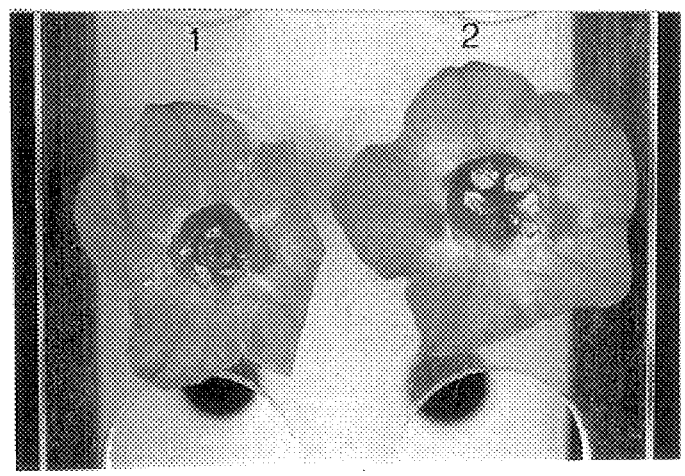
FIG. 7A
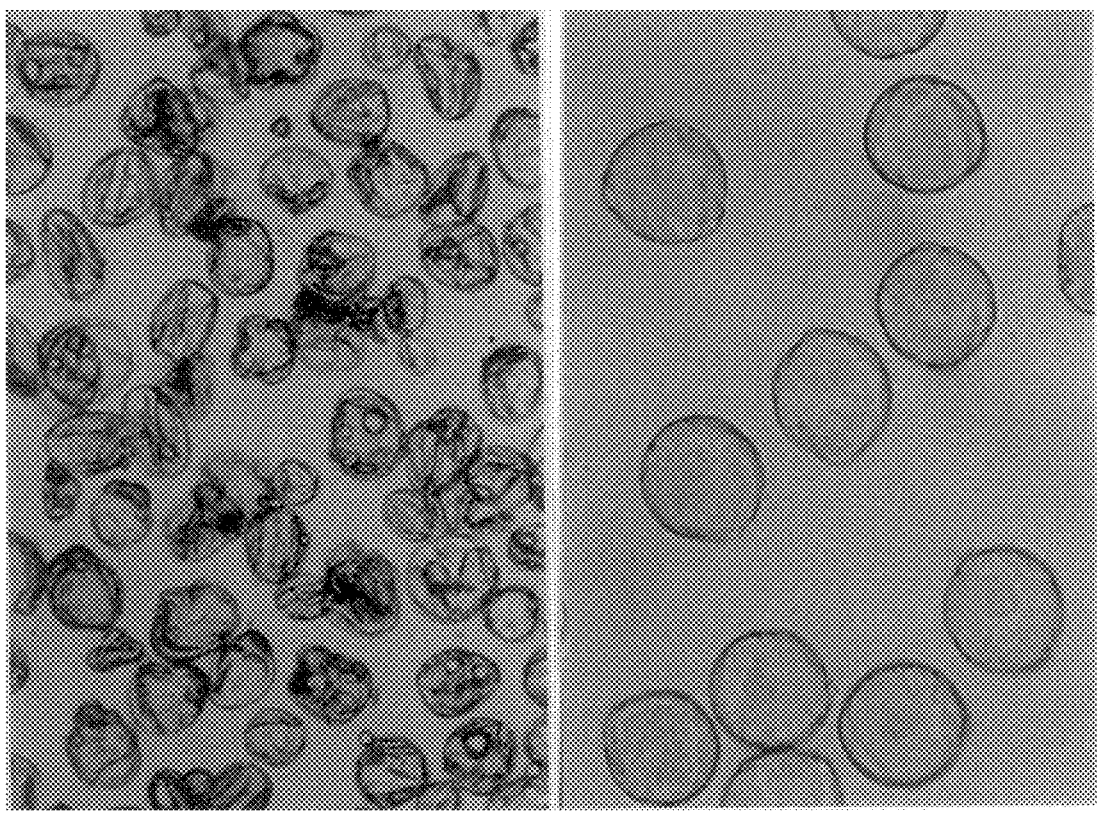
FIG. 7B
FIG. 7C

Intracellular localization of transgenic proteins by immunoblotting (SEQ ID NO: 1)

```
                                    GTCAACGTATTCTTCCCTGAAGAAACAGT
  1
 32 ATACTAACAATACTCACCCATTTCGATTTGATGTTGCCATACAAATAGATAACAAGCACAACACA

Met Leu Sea Leu Arg Gln Ser Ile Arg Phe Phe Lys Pro Ala Thr Arg Thr  17
 99 ATG CTT TCA CTA CGT CAA TCT ATA AGA TTT TTC AAG CCA GCC ACA AGA ACT

Leu Cys Ser Ser Arg Tyr Leu Leu Gln Gln Lys Pro Val Val Lys Thr Ala  34
151 TTG TGT AGC TCT AGA TAT CTG CTT CAG CAA AAA CCC GTG GTG AAA ACT GCC

Gln Asn Leu Ala Glu Val Asn Gly Pro Glu Thr Leu Ile Gly Pro Gly Ala  51
202 CAA AAC TTA GCA GAA GTT AAT GGT CCA GAA ACT TTG ATT GGT CCT GGT GCT

Lys Glu Gly Thr Arg Gly Ser Ser Arg Val Glu Met Leu Glu Gly Ala Lys  68
253 AAA GAG GGT ACC CGG GGA TCC TCT AGA GTC GAG ATG TTA GAA GGT GCT AAA

Ser Ile Gly Ala Ala Thr Ile Ile His Ser Leu Ala Gly Ala Ala Val Gly  85
304 TCA ATA GGT GCC GGA GCT GCT ACA ATT GCT CAT TCC GCC GGAGCT GCT GTC GGT

Ile Gly Asn Val Leu Ser Ser Leu Ile Tyr Ala Ile Leu Gly Val Ala Arg Asn Pro Ser 102
355 ATT GGA AAC GTC CTC AGT TCT TTG ATT TAT GCC ATT TTG GGC GTG GCG CGA AAT CCA TCA

Leu Ala Lys Gln Ser Phe Gly Tyr Ala Met Met Leu Phe Ala Leu Thr Glu 119
406 TTG GCT AAA CAA TCA TTT GGT TAT GCC ATG ATG CTG TTT GCT CTC ACC GAA

Ala Ile Ala Leu Phe Ala Pro Met Ala Phe Met Ala Ile Ser Phe Val Phe 136
457 GCT ATT GCA TTG TTT GCC CCA ATG GCC TTT ATG GCC ATC TCA TTC GTT TTC

Arg Ser His Lys Lys Ser Stop        142
508 CGA TCG CAT AAA AAG TCA TGA GATCAAAAAGAATGTGTGAATGTAGTTACAGATGTCGAC
```

Presequence COX IV-ATP 9 (unedited)

Figure 12

(SEQ ID NO: 12)  1       GTCAACGTATTCTTCTCCCTGAAGAAACAGT

32      ATACTAACAATACTCACCCATTCGATTTGATGTTGCCATACAAATAGATAACAAGCACAAGCACA

|     | Met | Leu | Sea | Leu | Arg | Gln | Ser | Ile | Arg | Phe | Phe | Lys | Pro | Ala | Thr | Arg | Thr | 17 |
|-----|-----|-----|-----|-----|-----|-----|-----|-----|-----|-----|-----|-----|-----|-----|-----|-----|-----|----|
| 99  | ATG | CTT | TCA | CTA | CGT | CAA | TCT | ATA | AGA | TTT | TTC | AAG | CCA | GCC | ACA | AGA | ACT |    |

|     | Leu | Cys | Ser | Ser | Arg | Tyr | Leu | Leu | Gln | Gln | Lys | Pro | Val | Val | Lys | Thr | Ala | 34 |
|-----|-----|-----|-----|-----|-----|-----|-----|-----|-----|-----|-----|-----|-----|-----|-----|-----|-----|----|
| 151 | TTG | TGT | AGC | TCT | AGA | TAT | CTG | CTT | CAG | CAA | AAA | CCC | GTG | GTG | AAA | ACT | GCC |    |

|     | Gln | Asn | Leu | Ala | Glu | Val | Asn | Gly | Pro | Glu | Thr | Leu | Ile | Gly | Pro | Gly | Ala | 51 |
|-----|-----|-----|-----|-----|-----|-----|-----|-----|-----|-----|-----|-----|-----|-----|-----|-----|-----|----|
| 202 | CAA | AAC | TTA | GCA | GAA | GTT | AAT | GGT | CCA | GAA | ACT | TTG | ATT | GGT | CCT | GGT | GCT |    |

|     | Lys | Glu | Gly | Thr | Arg | Gly | Ser | Ser | Arg | Val | Glu | Met | Leu | Glu | Ala | Lys | 68 |
|-----|-----|-----|-----|-----|-----|-----|-----|-----|-----|-----|-----|-----|-----|-----|-----|-----|----|
| 253 | AAA | GAG | GGT | ACC | CGG | GGA | TCC | TCT | AGA | GTC | GAG | ATG | TTA | GAA | GCT | AAA |    |

|     | Leu | Ile | Gly | Ile | Ala | Gly | Ala | Gly | Ser | Ser | Leu | Ser | Val | Gly | Ala | Val | Gly | 85 |
|-----|-----|-----|-----|-----|-----|-----|-----|-----|-----|-----|-----|-----|-----|-----|-----|-----|-----|----|
| 304 | TTA | ATA | GGT | ACA | ATT | GCT | GGA | GCT | AGT | TCT | TTG | TCA | GTC | GGA | GCT | GTC | GGT |    |

|     | Ile | Gly | Asn | Val | Phe | Ser | Ser | Leu | Tyr | Ala | Ile | His | Leu | Gly | Ala | Arg | Asn | Pro | Ser | 102 |
|-----|-----|-----|-----|-----|-----|-----|-----|-----|-----|-----|-----|-----|-----|-----|-----|-----|-----|-----|-----|-----|
| 355 | ATT | GGA | AAC | GTT | TTC | AGT | TCT | TTG | TAT | GCC | ATT | CAT | TCC | GTG | GCG | CGA | AAT | CCA | TCA |     |

|     | Leu | Ala | Lys | Gln | Leu | Phe | Ala | Leu | Met | Met | Ala | Phe | Leu | Gly | Phe | Ala | Leu | Thr | Glu | 119 |
|-----|-----|-----|-----|-----|-----|-----|-----|-----|-----|-----|-----|-----|-----|-----|-----|-----|-----|-----|-----|-----|
| 406 | TTG | GCT | AAA | CAA | TTA | TTT | GCC | CTA | ATG | ATG | GCC | TTT | TTG | GGC | TTT | GCT | CTC | ACC | GAA |     |

|     | Ala | Ile | Ala | Leu | Phe | Ala | Leu | Phe | Ala | Ala | Ile | Ile | Leu | Phe | Val | Phe | 136 |
|-----|-----|-----|-----|-----|-----|-----|-----|-----|-----|-----|-----|-----|-----|-----|-----|-----|-----|
| 457 | GCT | ATT | GCA | TTG | TTT | GCC | CTA | TTT | GCC | GCA | ATC | ATA | TTG | TTT | GTT | TTC |     |

Stop

508    TGA   TCGCATAAAAAGTCATGAGATCAAAAAGAATGTGTGAATGTAGTTACAGATGTCGAC

Presequence COX IV-ATP 9 (edited)

Figure 13

SEQUENCE LISTING

<160> NUMBER OF SEQ ID NOS: 13

<210> SEQ ID NO 1
<211> LENGTH: 568
<212> TYPE: DNA
<213> ORGANISM: WHEAT ATP9
<220> FEATURE:
<221> NAME/KEY: CDS
<222> LOCATION: (99)..(524)

<400> SEQUENCE: 1

```
gtcaacgtat tcttctccct gaagaaacag tatactaaca atactcaccc atttcgattt      60
tgatgttgcc atacaaatag ataacaagca caagcaca atg ctt tca cta cgt caa     116
                                         Met Leu Ser Leu Arg Gln
                                           1               5 tct ata aga ttt ttc aag cca gcc aca aga act ttg tgt agc tct aga       164
Ser Ile Arg Phe Phe Lys Pro Ala Thr Arg Thr Leu Cys Ser Ser Arg
                10                  15                  20 tat ctg ctt cag caa aaa ccc gtg gtg aaa act gcc caa aac tta gca       212
Tyr Leu Leu Gln Gln Lys Pro Val Val Lys Thr Ala Gln Asn Leu Ala
        25                  30                  35 gaa gtt aat ggt cca gaa act ttg att ggt cct ggt gct aaa gag ggt       260
Glu Val Asn Gly Pro Glu Thr Leu Ile Gly Pro Gly Ala Lys Glu Gly
 40                  45                  50 acc cgg gga tcc tct aga gtc gag atg tta gaa ggt gct aaa tca ata       308
Thr Arg Gly Ser Ser Arg Val Glu Met Leu Glu Gly Ala Lys Ser Ile
 55                  60                  65                  70 ggt gcc gga gct gct aca att gct tta gcc gga gct gct gtc ggt att       356
Gly Ala Gly Ala Ala Thr Ile Ala Leu Ala Gly Ala Ala Val Gly Ile
                 75                  80                  85 gga aac gtc ctc agt tct ttg att act tcc gtg gcg cga aat cca tca       404
Gly Asn Val Leu Ser Ser Leu Ile Thr Ser Val Ala Arg Asn Pro Ser
                 90                  95                 100 ttg gct aaa caa tca ttt ggt tat gcc att ttg ggc ttt gct ctc acc       452
Leu Ala Lys Gln Ser Phe Gly Tyr Ala Ile Leu Gly Phe Ala Leu Thr
        105                 110                 115 gaa gct att gca ttg ttt gcc cca atg atg gcc ttt ctg atc tca ttc       500
Glu Ala Ile Ala Leu Phe Ala Pro Met Met Ala Phe Leu Ile Ser Phe
 120                 125                 130 gtt ttc cga tcg cat aaa aag tca tgagatcaaa aagaaatgt gtgaatgtag       554
Val Phe Arg Ser His Lys Lys Ser
135                 140 ttacagatgt cgac                                                       568
```

<210> SEQ ID NO 2
<211> LENGTH: 142
<212> TYPE: PRT
<213> ORGANISM: WHEAT ATP9

<400> SEQUENCE: 2

```
Met Leu Ser Leu Arg Gln Ser Ile Arg Phe Phe Lys Pro Ala Thr Arg
 1               5                  10                  15

Thr Leu Cys Ser Ser Arg Tyr Leu Leu Gln Gln Lys Pro Val Val Lys
                20                  25                  30

Thr Ala Gln Asn Leu Ala Glu Val Asn Gly Pro Glu Thr Leu Ile Gly
        35                  40                  45

Pro Gly Ala Lys Glu Gly Thr Arg Gly Ser Ser Arg Val Glu Met Leu
    50                  55                  60
```

| | | | | | | | | | | | |
|---|---|---|---|---|---|---|---|---|---|---|---|
| Glu | Gly | Ala | Lys | Ser | Ile | Gly | Ala | Gly | Ala | Thr | Ile | Ala | Leu | Ala |
| | 65 | | | | 70 | | | | 75 | | | | 80 | |

Glu Gly Ala Lys Ser Ile Gly Ala Gly Ala Thr Ile Ala Leu Ala
 65                  70                  75                  80

Gly Ala Ala Val Gly Ile Gly Asn Val Leu Ser Ser Leu Ile Thr Ser
             85                  90                  95

Val Ala Arg Asn Pro Ser Leu Ala Lys Gln Ser Phe Gly Tyr Ala Ile
            100                 105                 110

Leu Gly Phe Ala Leu Thr Glu Ala Ile Ala Leu Phe Ala Pro Met Met
        115                 120                 125

Ala Phe Leu Ile Ser Phe Val Phe Arg Ser His Lys Lys Ser
    130                 135                 140

<210> SEQ ID NO 3
<211> LENGTH: 1106
<212> TYPE: DNA
<213> ORGANISM: WHEAT ATP9
<220> FEATURE:
<221> NAME/KEY: CDS
<222> LOCATION: (99)..(1103)

<400> SEQUENCE: 3

```
gtcaacgtat tcttctccct gaagaaacag tatactaaca atactcaccc atttcgattt      60
tgatgttgcc atacaaatag ataacaagca caagcaca atg ctt tca cta cgt caa     116
                                          Met Leu Ser Leu Arg Gln
                                            1               5 tct ata aga ttt ttc aag cca gcc aca aga act ttg tgt agc tct aga       164
Ser Ile Arg Phe Phe Lys Pro Ala Thr Arg Thr Leu Cys Ser Ser Arg
         10                  15                  20 tat ctg ctt cag caa aaa ccc gtg gtg aaa act gcc caa aac tta gca       212
Tyr Leu Leu Gln Gln Lys Pro Val Val Lys Thr Ala Gln Asn Leu Ala
     25                  30                  35 gaa gtt aat ggt cca gaa act ttg att ggt cct ggt gct aaa gag ggt       260
Glu Val Asn Gly Pro Glu Thr Leu Ile Gly Pro Gly Ala Lys Glu Gly
 40                  45                  50 acc cgg gga tcc tct aga gtc gag atg gat aat ttt atc cag aat ctg       308
Thr Arg Gly Ser Ser Arg Val Glu Met Asp Asn Phe Ile Gln Asn Leu
 55                  60                  65                  70 cct ggt gcc tac ccg gaa acc cca ttg gat caa ttt gcc att atc cca       356
Pro Gly Ala Tyr Pro Glu Thr Pro Leu Asp Gln Phe Ala Ile Ile Pro
             75                  80                  85 ata att gat ctt cat gtg ggc aac ttt tat tta tca ttt aca aat gaa       404
Ile Ile Asp Leu His Val Gly Asn Phe Tyr Leu Ser Phe Thr Asn Glu
         90                  95                 100 gtc ttg tat atg ctg ctc act gtc gtt tgg gtc gtt ttt ctt ttt ttt       452
Val Leu Tyr Met Leu Leu Thr Val Val Trp Val Val Phe Leu Phe Phe
     105                 110                 115 gtt gtt acg aaa aag gga ggt gga aag tca gtg cca aat gca tgg cca       500
Val Val Thr Lys Lys Gly Gly Gly Lys Ser Val Pro Asn Ala Trp Pro
 120                 125                 130 tcc ttg gtc gag ctt att tat gat ttc gtg ctg aac ctg gta aac gaa       548
Ser Leu Val Glu Leu Ile Tyr Asp Phe Val Leu Asn Leu Val Asn Glu
135                 140                 145                 150 caa ata ggt ggt ctt tcc gga aat gtg aaa caa aag ttt ttc cct cgc       596
Gln Ile Gly Gly Leu Ser Gly Asn Val Lys Gln Lys Phe Phe Pro Arg
             155                 160                 165 atc tcg gtc act ttt act ttt tcg tta ttt cgt aat ccc cag ggt atg       644
Ile Ser Val Thr Phe Thr Phe Ser Leu Phe Arg Asn Pro Gln Gly Met
         170                 175                 180 ata ccc ttt agc ttc aca gtg aca agt cat ttt ctc att act ttg gct       692
Ile Pro Phe Ser Phe Thr Val Thr Ser His Phe Leu Ile Thr Leu Ala
     185                 190                 195
```

-continued

```
ctt tca ttt tcc att ttt ata ggc att acg atc gtt gga ttt caa aga    740
Leu Ser Phe Ser Ile Phe Ile Gly Ile Thr Ile Val Gly Phe Gln Arg
    200                 205                 210 cat ggg ctt cat ttt ttt agc ttc tta tta cct gcg gga gtc cca ctg    788
His Gly Leu His Phe Phe Ser Phe Leu Leu Pro Ala Gly Val Pro Leu
215                 220                 225                 230 ccg tta gca cct ttc tta gta ctc ctt gag cta atc tct ata tgt ttt    836
Pro Leu Ala Pro Phe Leu Val Leu Leu Glu Leu Ile Ser Ile Cys Phe
                235                 240                 245 cgt gca tta agc tta gga ata cgt tta ttt gct aat atg atg gcc ggt    884
Arg Ala Leu Ser Leu Gly Ile Arg Leu Phe Ala Asn Met Met Ala Gly
            250                 255                 260 cat agt tta gta aag att tta agt ggg ttt gct tgg act atg cta ttt    932
His Ser Leu Val Lys Ile Leu Ser Gly Phe Ala Trp Thr Met Leu Phe
        265                 270                 275 ctg aat aat att ttc tat ttc ata gga gat ctt ggt ccc tta ttt ata    980
Leu Asn Asn Ile Phe Tyr Phe Ile Gly Asp Leu Gly Pro Leu Phe Ile
    280                 285                 290 gtt cta gca tta acc ggt ctg gaa tta ggt gta gct ata tca caa gct   1028
Val Leu Ala Leu Thr Gly Leu Glu Leu Gly Val Ala Ile Ser Gln Ala
295                 300                 305                 310 cat gtt tct acg atc tca att tgt att tac ttg aat gat gct aca aat   1076
His Val Ser Thr Ile Ser Ile Cys Ile Tyr Leu Asn Asp Ala Thr Asn
                315                 320                 325 ctc act caa aat gag tca ttt cat aat tga                           1106
Leu Thr Gln Asn Glu Ser Phe His Asn
            330                 335
```

<210> SEQ ID NO 4
<211> LENGTH: 335
<212> TYPE: PRT
<213> ORGANISM: WHEAT ATP9

<400> SEQUENCE: 4

```
Met Leu Ser Leu Arg Gln Ser Ile Arg Phe Phe Lys Pro Ala Thr Arg
  1               5                  10                  15

Thr Leu Cys Ser Ser Arg Tyr Leu Leu Gln Gln Lys Pro Val Val Lys
             20                  25                  30

Thr Ala Gln Asn Leu Ala Glu Val Asn Gly Pro Glu Thr Leu Ile Gly
         35                  40                  45

Pro Gly Ala Lys Glu Gly Thr Arg Gly Ser Ser Arg Val Glu Met Asp
     50                  55                  60

Asn Phe Ile Gln Asn Leu Pro Gly Ala Tyr Pro Glu Thr Pro Leu Asp
 65                  70                  75                  80

Gln Phe Ala Ile Ile Pro Ile Ile Asp Leu His Val Gly Asn Phe Tyr
                 85                  90                  95

Leu Ser Phe Thr Asn Glu Val Leu Tyr Met Leu Leu Thr Val Val Leu
            100                 105                 110

Val Val Phe Leu Phe Phe Val Val Thr Lys Lys Gly Gly Gly Lys Ser
        115                 120                 125

Val Pro Asn Ala Trp Pro Ser Leu Val Glu Leu Ile Tyr Asp Phe Val
    130                 135                 140

Leu Asn Leu Val Asn Glu Gln Ile Gly Gly Leu Ser Gly Asn Val Lys
145                 150                 155                 160

Gln Lys Phe Phe Pro Arg Ile Ser Val Thr Phe Thr Phe Ser Leu Phe
                165                 170                 175

Arg Asn Pro Gln Gly Met Ile Pro Phe Ser Phe Thr Val Thr Ser His
```

```
                        180                 185                 190
Phe Leu Ile Thr Leu Ala Leu Ser Phe Ser Ile Phe Ile Gly Ile Thr
            195                 200                 205

Ile Val Gly Phe Gln Arg His Gly Leu His Phe Ser Phe Leu Leu
        210                 215                 220

Pro Ala Gly Val Pro Leu Pro Leu Ala Pro Phe Leu Val Leu Glu
225                 230                 235                 240

Leu Ile Ser Ile Cys Phe Arg Ala Leu Ser Leu Gly Ile Arg Leu Phe
                245                 250                 255

Ala Asn Met Met Ala Gly His Ser Leu Val Lys Ile Leu Ser Gly Phe
            260                 265                 270

Ala Trp Thr Met Leu Phe Leu Asn Asn Ile Phe Tyr Phe Ile Gly Asp
        275                 280                 285

Leu Gly Pro Leu Phe Ile Val Leu Ala Leu Thr Gly Leu Glu Leu Gly
    290                 295                 300

Val Ala Ile Ser Gln Ala His Val Ser Thr Ile Ser Ile Cys Ile Tyr
305                 310                 315                 320

Leu Asn Asp Ala Thr Asn Leu Thr Gln Asn Glu Ser Phe His Asn
                325                 330                 335

<210> SEQ ID NO 5
<211> LENGTH: 1067
<212> TYPE: DNA
<213> ORGANISM: WHEAT ATP9
<220> FEATURE:
<221> NAME/KEY: CDS
<222> LOCATION: (99)..(1064)

<400> SEQUENCE: 5
gtcaacgtat tcttctccct gaagaaacag tatactaaca atactcaccc atttcgattt      60
tgatgttgcc atacaaatag ataacaagca caagcaca atg ctt tca cta cgt caa     116
                                          Met Leu Ser Leu Arg Gln
                                            1               5 tct ata aga ttt ttc aag cca gcc aca aga act ttg tgt agc tct aga       164
Ser Ile Arg Phe Phe Lys Pro Ala Thr Arg Thr Leu Cys Ser Ser Arg
         10                  15                  20 tat ctg ctt cag caa aaa ccc gtg gtg aaa act gcc caa aac tta gca       212
Tyr Leu Leu Gln Gln Lys Pro Val Val Lys Thr Ala Gln Asn Leu Ala
     25                  30                  35 gaa gtt aat ggt cca gaa act ttg att ggt cct ggt gct aaa gag ggt       260
Glu Val Asn Gly Pro Glu Thr Leu Ile Gly Pro Gly Ala Lys Glu Gly
 40                  45                  50 acc cgg gga tcc tct aga gtc gag atg att ctt cgt tca tta tca tgt       308
Thr Arg Gly Ser Ser Arg Val Glu Met Ile Leu Arg Ser Leu Ser Cys
 55                  60                  65                  70 cga ttc ttc aga atc gct ctt tgt gat gct gcg gaa cca tgg caa tta       356
Arg Phe Phe Arg Ile Ala Leu Cys Asp Ala Ala Glu Pro Trp Gln Leu
             75                  80                  85 gga tct caa gac gca gca aca cct atg atg caa gga atc att gac tta      404
Gly Ser Gln Asp Ala Ala Thr Pro Met Met Gln Gly Ile Ile Asp Leu
         90                  95                 100 cat cac gat atc ttt ttc ttc ctc att ctt att ttg gtt ttc gta tca      452
His His Asp Ile Phe Phe Phe Leu Ile Leu Ile Leu Val Phe Val Ser
     105                 110                 115 cgg atg ttg gtt cgc gct tta tgg cat ttc aac gag caa act aat cca      500
Arg Met Leu Val Arg Ala Leu Trp His Phe Asn Glu Gln Thr Asn Pro
 120                 125                 130 atc cca caa agg att gtt cat gga act act atg gaa att att cgg acc      548
```

```
Ile Pro Gln Arg Ile Val His Gly Thr Thr Met Glu Ile Ile Arg Thr
135                 140                 145                 150 ata ttt cca agt gtc att ctt ttg ttc att gct ata cca tcg ttt gct     596
Ile Phe Pro Ser Val Ile Leu Leu Phe Ile Ala Ile Pro Ser Phe Ala
                155                 160                 165 ctg tta tac tca atg gac ggg gta tta gta gat cca gcc att act atc     644
Leu Leu Tyr Ser Met Asp Gly Val Leu Val Asp Pro Ala Ile Thr Ile
            170                 175                 180 aaa gct att gga cat caa tgg tat cgg act tat gag tat tcg gac tat     692
Lys Ala Ile Gly His Gln Trp Tyr Arg Thr Tyr Glu Tyr Ser Asp Tyr
        185                 190                 195 aac agt tcc gat gaa cag tca ctc act ttt gac agt tat acg att cca     740
Asn Ser Ser Asp Glu Gln Ser Leu Thr Phe Asp Ser Tyr Thr Ile Pro
200                 205                 210 gaa gat gat cca gaa ttg ggt caa tca cgt tta tta gaa gtt gac aat     788
Glu Asp Asp Pro Glu Leu Gly Gln Ser Arg Leu Leu Glu Val Asp Asn
215                 220                 225                 230 aga gtg gtt gta cca gcc aaa act cat cta cgt atg att gta aca ccc     836
Arg Val Val Val Pro Ala Lys Thr His Leu Arg Met Ile Val Thr Pro
                235                 240                 245 gct gat gta cct cat agt tgg gct gta cct tcc tca ggt gtc aaa tgt     884
Ala Asp Val Pro His Ser Trp Ala Val Pro Ser Ser Gly Val Lys Cys
            250                 255                 260 gat gct gta cct ggt cgt tca aat ctt acc ttc atc tcg gta caa cga     932
Asp Ala Val Pro Gly Arg Ser Asn Leu Thr Phe Ile Ser Val Gln Arg
        265                 270                 275 gaa gaa gtt tca tat ggt cag tgc agt gag att cgt gga act aat cat     980
Glu Glu Val Ser Tyr Gly Gln Cys Ser Glu Ile Arg Gly Thr Asn His
    280                 285                 290 gcc ttt acg cct atc gtc gta gaa gca gtg act ttg aaa gat tat gcg    1028
Ala Phe Thr Pro Ile Val Val Glu Ala Val Thr Leu Lys Asp Tyr Ala
295                 300                 305                 310 gat tgg gta tcc aat caa tta atc ctc caa acc aac taa                1067
Asp Trp Val Ser Asn Gln Leu Ile Leu Gln Thr Asn
                315                 320

<210> SEQ ID NO 6
<211> LENGTH: 322
<212> TYPE: PRT
<213> ORGANISM: WHEAT ATP9

<400> SEQUENCE: 6

Met Leu Ser Leu Arg Gln Ser Ile Arg Phe Phe Lys Pro Ala Thr Arg
  1               5                  10                  15

Thr Leu Cys Ser Ser Arg Tyr Leu Leu Gln Gln Lys Pro Val Val Lys
                20                  25                  30

Thr Ala Gln Asn Leu Ala Glu Val Asn Gly Pro Glu Thr Leu Ile Gly
            35                  40                  45

Pro Gly Ala Lys Glu Gly Thr Arg Gly Ser Ser Arg Val Glu Met Ile
        50                  55                  60

Leu Arg Ser Leu Ser Cys Arg Phe Phe Arg Ile Ala Leu Cys Asp Ala
 65                  70                  75                  80

Ala Glu Pro Trp Gln Leu Gly Ser Gln Asp Ala Ala Thr Pro Met Met
                85                  90                  95

Gln Gly Ile Ile Asp Leu His His Asp Ile Phe Phe Leu Ile Leu
            100                 105                 110

Ile Leu Val Phe Val Ser Arg Met Leu Val Arg Ala Leu Trp His Phe
        115                 120                 125
```

-continued

Asn Glu Gln Thr Asn Pro Ile Pro Gln Arg Ile Val His Gly Thr Thr
    130                 135                 140

Met Glu Ile Ile Arg Thr Ile Phe Pro Ser Val Ile Leu Leu Phe Ile
145                 150                 155                 160

Ala Ile Pro Ser Phe Ala Leu Leu Tyr Ser Met Asp Gly Val Leu Val
                165                 170                 175

Asp Pro Ala Ile Thr Ile Lys Ala Ile Gly His Gln Trp Tyr Arg Thr
            180                 185                 190

Tyr Glu Tyr Ser Asp Tyr Asn Ser Ser Asp Glu Gln Ser Leu Thr Phe
        195                 200                 205

Asp Ser Tyr Thr Ile Pro Glu Asp Asp Pro Glu Leu Gly Gln Ser Arg
    210                 215                 220

Leu Leu Glu Val Asp Asn Arg Val Val Val Pro Ala Lys Thr His Leu
225                 230                 235                 240

Arg Met Ile Val Thr Pro Ala Asp Val Pro His Ser Trp Ala Val Pro
                245                 250                 255

Ser Ser Gly Val Lys Cys Asp Ala Val Pro Gly Arg Ser Asn Leu Thr
            260                 265                 270

Phe Ile Ser Val Gln Arg Glu Glu Val Ser Tyr Gly Gln Cys Ser Glu
        275                 280                 285

Ile Arg Gly Thr Asn His Ala Phe Thr Pro Ile Val Val Glu Ala Val
    290                 295                 300

Thr Leu Lys Asp Tyr Ala Asp Trp Val Ser Asn Gln Leu Ile Leu Gln
305                 310                 315                 320

Thr Asn

<210> SEQ ID NO 7
<211> LENGTH: 243
<212> TYPE: DNA
<213> ORGANISM: WHEAT ATP9

<400> SEQUENCE: 7
atgttagaag gtgctaaatc aataggtgcc ggagctgcta caattgcttt agccggagct      60
gctgtcggta ttggaaacgt cctcagttct tgattcatt ccgtggcgcg aaatccatca     120
ttggctaaac aatcatttgg ttatgccatt tgggctttg ctctcaccga agctattgca     180
ttgtttgccc caatgatggc ctttctgatc tcattcgttt ccgatcgca taaaaagtca     240 tga                                                                  243

<210> SEQ ID NO 8
<211> LENGTH: 822
<212> TYPE: DNA
<213> ORGANISM: WHEAT ATP9

<400> SEQUENCE: 8
atggataatt ttatccagaa tctgcctggt gcctacccgg aaaccccatt ggatcaattt      60
gccattatcc caataattga tcttcatgtg ggcaactttt atttatcatt acaaatgaa     120 gtcttgtata tgctgctcac tgtcgttttg gtcgtttttc ttttttttgt tgttacgaaa     180
aagggaggta gaaagtcagt gccaaatgca tggcaatcct tggtcgagct tatttatgat     240
ttcgtgctga acctggtaaa cgaacaaata ggtggtcttt ccggaaatgt gaaacaaaag     300 ttttttccctc gcatctcggt cacttttact ttttcgttat ttcgtaatcc ccagggtatg     360 ataccctta gcttcacagt gacaagtcat tttctcatta ctttggctct ttcatttttcc     420 atttttatag gcattacgat cgttggattt caaagacatg gcttcatttt ttttagcttc     480

```
ttattacctg cgggagtccc actgccgtta gcacctttct tagtactcct tgagctaatc    540
tcttattgtt ttcgtgcatt aagcttagga atacgtttat ttgctaatat gatggccggt    600
catagtttag taaagatttt aagtgggttt gcttggacta tgctatttct gaataatatt    660
ttctatttca taggagatct tggtcccttta tttatagttc tagcattaac cggtctggaa    720
ttaggtgtag ctatatcaca agctcatgtt tctacgatct caatttgtat ttacttgaat    780
gatgctacaa atctccatca aaatgagtca tttcataatt ga                       822
```

<210> SEQ ID NO 9
<211> LENGTH: 783
<212> TYPE: DNA
<213> ORGANISM: WHEAT ATP9

<400> SEQUENCE: 9

```
atgattcttc gttcattatc atgtcgattc ttcacaatcg ctctttgtga tgctgcggaa     60
ccatggcaat taggatctca agacgcagca acacctatga tgcaaggaat cattgactta    120
catcacgata tcttttttctt cctcattctt attttggttt tcgtatcacg gatgttggtt    180
cgcgctttat ggcatttcaa cgagcaaact aatccaatcc cacaaaggat tgttcatgga    240
actactatgg aaattattcg gaccatattt ccaagtgtca ttcttttgtt cattgctata    300
ccatcgtttg ctctgttata ctcaatggac ggggtattag tagatccagc cattactatc    360
aaagctattg gacatcaatg gtatcggact tatgagtatt cggactataa cagttccgat    420
gaacagtcac tcacttttga cagttatacg attccagaag atgatccaga attgggtcaa    480
tcacgtttat tagaagttga caatagagtg gttgtaccag ccaaaactca tctacgtatg    540
attgtaacac ccgctgatgt acctcatagt tgggctgtac cttcctcagg tgtcaaatgt    600
gatgctgtac ctggtcgttc aaatcttacc ttcatctcgg tacaacgaga aggagtttac    660
tatggtcagt gcagtgagat tcgtggaact aatcatgcct ttacgcctat cgtcgtagaa    720
gcagtgactt tgaaagatta tgcggattgg gtatccaatc aattaatcct ccaaaccaac    780
taa                                                                  783
```

<210> SEQ ID NO 10
<211> LENGTH: 19
<212> TYPE: DNA
<213> ORGANISM: WHEAT ATP9

<400> SEQUENCE: 10

```
cactacgtca atctataag                                                  19
```

<210> SEQ ID NO 11
<211> LENGTH: 19
<212> TYPE: DNA
<213> ORGANISM: WHEAT ATP9

<400> SEQUENCE: 11

```
tatgctcaac acatgagcg                                                  19
```

<210> SEQ ID NO 12
<211> LENGTH: 568
<212> TYPE: DNA
<213> ORGANISM: WHEAT ATP9
<220> FEATURE:
<221> NAME/KEY: CDS
<222> LOCATION: (99)..(506)

<400> SEQUENCE: 12

-continued

```
gtcaacgtat tcttctccct gaagaaacag tatactaaca atactcaccc atttcgattt        60
tgatgttgcc atacaaatag ataacaagca caagcaca atg ctt tca cta cgt caa       116
                                          Met Leu Ser Leu Arg Gln
                                            1               5 tct ata aga ttt ttc aag cca gcc aca aga act ttg tgt agc tct aga         164
Ser Ile Arg Phe Phe Lys Pro Ala Thr Arg Thr Leu Cys Ser Ser Arg
            10                  15                  20 tat ctg ctt cag caa aaa ccc gtg gtg aaa act gcc caa aac tta gca         212
Tyr Leu Leu Gln Gln Lys Pro Val Val Lys Thr Ala Gln Asn Leu Ala
        25                  30                  35 gaa gtt aat ggt cca gaa act ttg att ggt cct ggt gct aaa gag ggt         260
Glu Val Asn Gly Pro Glu Thr Leu Ile Gly Pro Gly Ala Lys Glu Gly
    40                  45                  50 acc cgg gga tcc tct aga gtc gag atg tta gaa ggt gct aaa tta ata         308
Thr Arg Gly Ser Ser Arg Val Glu Met Leu Glu Gly Ala Lys Leu Ile
55                  60                  65                  70 ggt gcc gga gct gct aca att gct tta gcc gga gct gct gtc ggt att         356
Gly Ala Gly Ala Ala Thr Ile Ala Leu Ala Gly Ala Ala Val Gly Ile
                75                  80                  85 gga aac gtt ttc agt tct ttg att cat tcc gtg gcg cga aat cca tca         404
Gly Asn Val Phe Ser Ser Leu Ile His Ser Val Ala Arg Asn Pro Ser
        90                  95                 100 ttc gct aaa caa tta ttt ggt tat gcc att ttg ggc ttt gct ctc acc         452
Phe Ala Lys Gln Leu Phe Gly Tyr Ala Ile Leu Gly Phe Ala Leu Thr
    105                 110                 115 gaa gct att gca ttg ttt gcc cta atg atg gcc ttt ttg atc tta ttc         500
Glu Ala Ile Ala Leu Phe Ala Leu Met Met Ala Phe Leu Ile Leu Phe
120                 125                 130 gtt ttc tgatcgcata aaagtcatg agatcaaaaa agaaatgtgt gaatgtagtt           556
Val Phe
135 acagatgtcg ac                                                           568

<210> SEQ ID NO 13
<211> LENGTH: 136
<212> TYPE: PRT
<213> ORGANISM: WHEAT ATP9

<400> SEQUENCE: 13

Met Leu Ser Leu Arg Gln Ser Ile Arg Phe Phe Lys Pro Ala Thr Arg
  1               5                  10                  15

Thr Leu Cys Ser Ser Arg Tyr Leu Leu Gln Gln Lys Pro Val Val Lys
                20                  25                  30

Thr Ala Gln Asn Leu Ala Glu Val Asn Gly Pro Glu Thr Leu Ile Gly
            35                  40                  45

Pro Gly Ala Lys Glu Gly Thr Arg Gly Ser Ser Arg Val Glu Met Leu
        50                  55                  60

Glu Gly Ala Lys Leu Ile Gly Ala Gly Ala Ala Thr Ile Ala Leu Ala
 65                  70                  75                  80

Gly Ala Ala Val Gly Ile Gly Asn Val Phe Ser Ser Leu Ile His Ser
                85                  90                  95

Val Ala Arg Asn Pro Ser Phe Ala Lys Gln Leu Phe Gly Tyr Ala Ile
            100                 105                 110
```

```
                                    -continued

Leu Gly Phe Ala Leu Thr Glu Ala Ile Ala Leu Phe Ala Leu Met Met
        115                 120                 125

Ala Phe Leu Ile Leu Phe Val Phe
    130             135
```

TRANSGENIC PLANTS INCLUDING A TRANSGENE CONSISTING OF A HYBRID NUCLEIC ACID SEQUENCE, COMPRISING AT LEAST ONE UNEDITED MITOCHONDRIAL GENE FRAGMENT FROM HIGHER PLANTS AND PROCESS FOR PRODUCING THEM

This application is a divisional of application Ser. No. 08/505,218 filed Nov. 3, 1995, now U.S. Pat. No. 5,914,447, which is a 371 of PCT/FR94/00162 filed Feb. 15, 1994.

FIELD OF THE INVENTION

The present invention relates to hybrid nucleic acid sequences, comprising at least the coding region of an unedited mitochondrial gene from higher plants and allowing the control of male fertility in plants containing the said sequences, to the transgenic plants having such sequences, as well as to a method for producing transgenic male-sterile plants and to a method for restoring male-fertile plants.

BACKGROUND OF THE INVENTION

The control of male fertility in plants is one of the key problems for obtaining hybrids, and more particularly male-sterile lines which are of agronomic interest especially for controlling and improving seeds. Indeed, the large scale production of hybrid seeds with controlled characteristics is a real challenge since many crops have both male and female reproductive organs (stamens and pistils). This causes a high rate of self-pollination and makes difficult the control of crossings between lines for obtaining the desired hybrids.

In order to allow non-inbred crossings to be obtained which make it possible to produce hybrid seeds having advantageous properties, the inventors have developed new transgenic male-sterile plants capable of being restored and which facilitate the development of hybrid crops.

Cytoplasmic male sterility (MCS) is characterized by non-formation of the pollen after meiosis.

In alloplasmic systems, MCS is due to a nucleus-cytoplasm incompatibility which may occur at several levels: replication of DNA, transcription of genes, maturation of transcripts, translation or assembly of multiprotein complexes.

From the observations made on maize and petunia (Dewey R. E. et al., Cell, 1986, 44, 439; Young E. G. et al., Cell. 1987, 50, 41), comes the hypothesis that MCS is due to a deficiency in the mitochondrial bioenergetic machinery. Indeed, MCS manifests itself by a reduction in the ATP and NADP levels. At the cellular level, this deficiency is correlated with degeneration of the cells of the anther lawn, while having no effect on the development of the plant.

A number of methods have been proposed in the prior art for obtaining male-sterile plants.

There may be mentioned especially the backcrossings which lead to the substitution of the nuclear genome of a species by another genome and this, in the cytoplasmic environment of the first species (alloplasmy); this substitution may also appear spontaneously in field crops. MCS can also be obtained by protoplast fusion (Lonsdale D. M., Genetic Engineering, 1987, 6, 47).

In all these situations, the results are not reliable or reproducible; furthermore, in all cases, the manipulations are long, tedious and often difficult to control.

Male-sterile plants have also been obtained by transgenosis, with the aid of a gene encoding an RNAse, under the control of an anther-specific promoter (Mariani C. et al., Nature, 1990, 347, 737). This transgene, when expressed, has a toxic effect on the cell insofar as the endogenos RNAs are degraded, thereby causing cell death.

Another system, which also introduces a new artificial and destructive function, has been described by Worrall D. et al., (The Plant Cell, 1992, 4, 759–771) (callase system) and has the same disadvantages as the RNAse system.

Other methodologies have also been proposed for obtaining male-sterile plants; there may be mentioned especially the techniques which take advantage of the disruption of certain metabolic pathways (Van de Meer I. M. et al., The Plant Cell, 1992, 4, 253–262) (expression of a chalcone synthase antisense gene) or the techniques involving asymmetric somatic hybridization (Melchers C. et al., Proc. Natl. Acad. Sci. USA, 1992, 89, 6832–6836) to bring into contact, as in alloplasmic male-sterile lines, the cytoplasm of a donor individual and the nucleus of a recipient partner. The latter two processes have the major disadvantage of being highly unpredictable as regards the desired objective, namely the obtaining of male-sterile plants which makes it possible to control reproduction in these plants.

SUMMARY OF THE INVENTION

The Applicant consequently set itself the objective of obtaining transgenic male-sterile plants in a controlled, reliable and reproducible manner which are capable of being used in agronomic programmes of seed improvement.

The subject of the present invention is transgenic plants having in their nuclei an expressible hybrid sequence (transgene) comprising at least one coding region of an unedited mitochondrial gene from higher plants and a sequence capable of transferring the protein expressed by the said coding region to the mitochondrion, which plants are characterized in that:

the coding regions of the unedited mitochondrial genes are chosen from among the genes encoding a protein of the ATP synthase complex which are chosen from among the wheat ATP9 gene fragment, of the following formula I:

(Seq ID No: 7)
ATG TTA GAA GGT GCT AAA TCA ATA GGT GCC GGA GCT

GCT ACA ATT GCT TTA GCC GGA GCT GCT GTC GGT ATT

GGA AAC GTC CTC AGT TCT TTG ATT CAT TCC GTG GCG

CGA AAT CCA TCA TTG GCT AAA CAA TCA TTT GGT TAT

GCC ATT TTG GGC TTT GCT CTC ACC GAA GCT ATT GCA

TTG TTT GCC CCA ATG ATG GCC TTT CTG ATC TCA TTC

GTT TTC CGA TCG CAT AAA AAG TCA TGA or the ATP6 gene, or from among the genes encoding a protein of the respiratory chain which are chosen from among the genes for subunits 1 to 7 of NAD dehydrogenase, the gene for apocytochrome b and the genes for subunits I, II or III of cytochrome oxidase and the sequence capable of transferring the said expressed protein to the mitochondrion is selected from the group consisting of the fragments encoding yeast tryptophanyl tRNA synthetase (SCHMITZ, U. K. et al., 1989, The Plant Cell, 1, 783-791), and the .beta. subunit of Nicotiana plumbaginifolia ATPase (BOUTRY et al., 1987, Nature, 328:340–342), and the maize ATP/ADP translocator (BATHGATE et al., 1989, Eur. J. Biochem., 183:303–310) or a 303 base pair EcoRI/KpnI fragment including codons 1 to 62 of subunit IV of yeast cytochrome oxidase (MAARSE et al., 1984, EMBO J., 3, 2831–2837),
which hybrid sequence is capable of modifying male fertility in plants having incorporated the said transgene while not modifying the other phenotypic characteristics of the said plants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A–7C depict flowers from transgenic plants (7A1) and normal plants (7A2) and pollen grains from transgenic plants (7B) and from normal plants (7C).

FIG. 12 depicts the Presequence of COX IV-ATP 9 (unedited).

FIG. 13 depicts the Presequence COX IV-ATP 9 (edited).

DETAILED DESCRIPTION OF THE INVENTION

Figure 1:
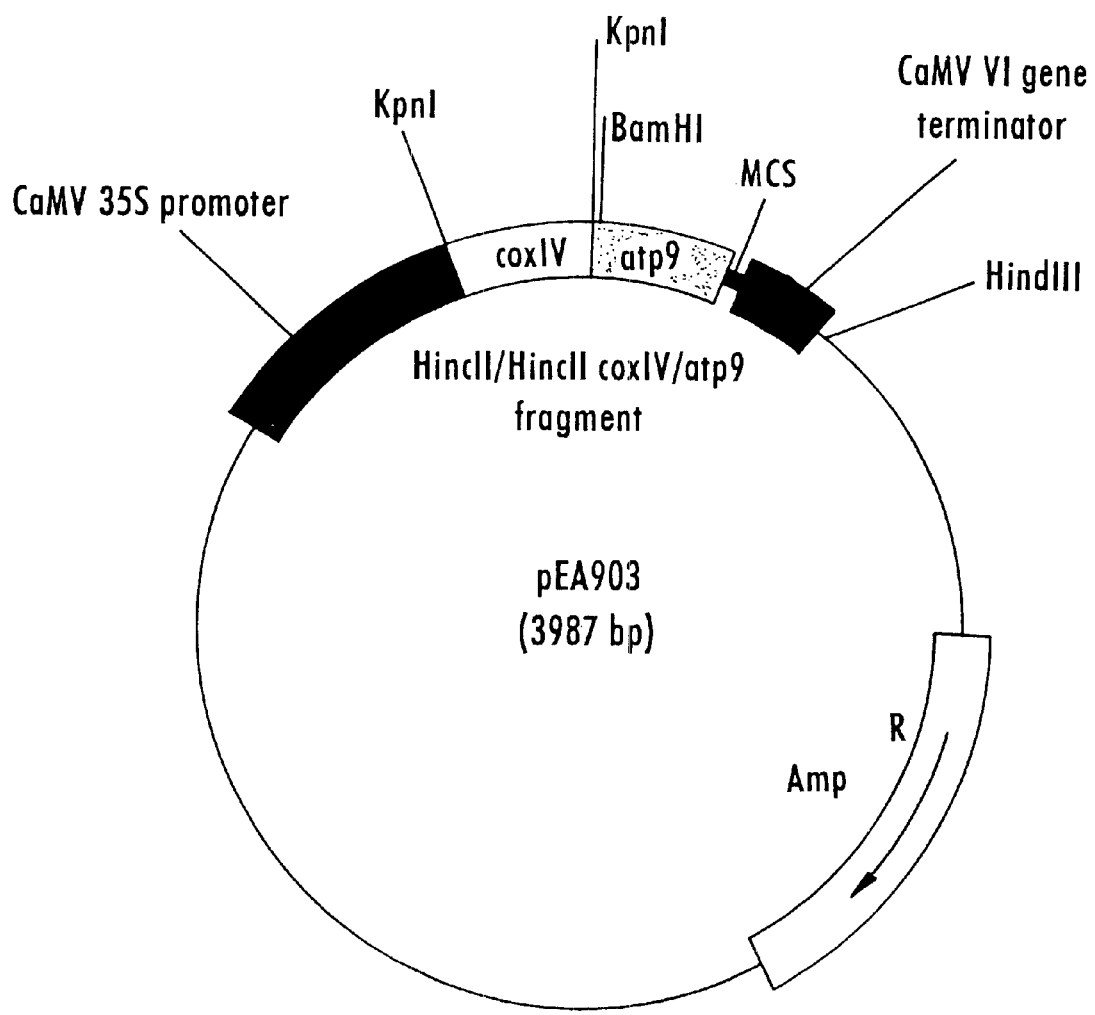
FIG. 1 depicts plasmid pEA903.

According to an advantageous embodiment of the said transgenic plants, the said hybrid nucleic acid sequence comprises the coding region of formula I of the gene encoding the unedited form of wheat ATP9, with which is associated as transfer sequence, codons 1 to 62 of the presequence of subunit IV of the yeast cytochrome oxidase (cox IV) (SEQ ID No. 1).

According to another advantageous embodiment of the said transgenic plants, the said hybrid nucleic acid sequence comprises the fragment of the region encoding the unedited form of wheat ATP6, of the following formula II:

(SEQ ID NO: 8)
ATG GAT AAT TTT ATC CAG AAT CTG CCT GGT GCC TAC

CCG GAA ACC CCA TTG GAT CAA TTT GCC ATT ATC CCA

ATA ATT GAT CTT CAT GTG GGC AAC TTT TAT TTA TCA

TTT ACA AAT GAA GTC TTG TAT ATG CTG CTC ACT GTC

GTT TTG GTC GTT TTT CTT TTT TTT GTT GTT ACG AAA

AAG GGA GGT GGA AAG TCA GTG CCA AAT GCA TGG CAA

TCC TTG GTC GAG CTT ATT TAT GAT TTC GTG CTG AAC

CTG GTA AAC GAA CAA ATA GGT GGT CTT TCC GGA AAT

GTG AAA CAA AAG TTT TTC CCT CGC ATC TCG GTC ACT

TTT ACT TTT TCG TTA TTT CGT AAT CCC CAG GGT ATG

ATA CCC TTT AGC TTC ACA GTG ACA AGT CAT TTT CTC

ATT ACT TTG GCT CTT TCA TTT TCC ATT TTT ATA GGC

ATT ACG ATC GTT GGA TTT CAA AGA CAT GGG CTT CAT

TTT TTT AGC TTC TTA TTA CCT GCG GGA GTC CCA CTG

CCG TTA GCA CCT TTC TTA GTA CTC CTT GAG CTA ATC

TCT TAT TGT TTT CGT GCA TTA AGC TTA GGA ATA CGT

TTA TTT GCT AAT ATG ATG GCC GGT CAT AGT TTA GTA

AAG ATT TTA AGT GGG TTT GCT TGG ACT ATG CTA TTT

CTG AAT AAT ATT TTC TAT TTC ATA GGA GAT CTT GGT

CCC TTA TTT ATA GTT CTA GCA TTA ACC GGT CTG GAA

TTA GGT GTA GCT ATA TCA CAA GCT CAT GTT TCT ACG

ATC TCA ATT TGT ATT TAC TTG AAT GAT GCT ACA AAT

CTC CAT CAA AAT GAG TCA TTT CAT AAT TGA, with which is associated as transfer sequence, codons 1 to 62 of the presequence of subunit IV of yeast cytochrome oxidase (cox IV) (SEQ ID No. 3).

According to another advantageous embodiment of the said transgenic plants, the said hybrid nucleic acid sequence comprises the fragment of the region encoding the unedited form of cox II of the following formula III:

(SEQ ID NO: 9)
ATG ATT CTT CGT TCA TTA TCA TGT CGA TTC TTC ACA

ATC GCT CTT TGT GAT GCT GCG GAA CCA TGG CAA TTA

GGA TCT CAA GAC GCA GCA ACA CCT ATG ATG CAA GGA

ATC ATT GAC TTA CAT CAC GAT ATC TTT TTC CTC

ATT CTT ATT TTG GTT TTC GTA TCA CGG ATG TTG GTT

CGC GCT TTA TGG CAT TTC AAC GAG CAA ACT AAT CCA

ATC CCA CAA AGG ATT GTT CAT GGA ACT ACT ATG GAA

ATT ATT CGG ACC ATA TTT CCA AGT GTC ATT CTT TTG

TTC ATT GCT ATA CCA TCG TTT GCT CTG TTA TAC TCA

ATG GAC GGG GTA TTA GTA GAT CCA GCC ATT ACT ATC

AAA GCT ATT GGA CAT CAA TGG TAT CGG ACT TAT GAG

TAT TCG GAC TAT AAC AGT TCC GAT GAA CAG TCA CTC

ACT TTT GAC AGT TAT ACG ATT CCA GAA GAT GAT CCA

GAA TTG GGT CAA TCA CGT TTA TTA GAA GTT GAC AAT

AGA GTG GTT GTA CCA GCC AAA ACT CAT CTA CGT ATG

ATT GTA ACA CCC GCT GAT GTA CCT CAT AGT TGG GCT

GTA CCT TCC TCA GGT GTC AAA TGT GAT GCT GTA CCT

GGT CGT TCA AAT CTT ACC TTC ATC TCG GTA CAA CGA

-continued

```
GAA GGA GTT TAC TAT GGT CAG TGC AGT GAG ATT CGT

GGA ACT AAT CAT GCC TTT ACG CCT ATC GTC GTA GAA

GCA GTG ACT TTG AAA GAT TAT GCG GAT TGG GTA TCC

AAT GAA TTA ATC CTC CAA ACC AAC TAA,
``` with which is associated as transfer sequence, codons 1 to 62 of the presequence of subunit IV of yeast cytochrome oxidase (cox IV) (SEQ ID No. 5).

The plants having incorporated the transgene in accordance with the invention (transgenic plants) are generally selected from plants which are of agronomic, medical or industrial interest. More precisely, any transformable and regenerable plant can constitute the raw material for obtaining a transgenic plant in accordance with the invention.

For the purposes of the present invention, transformable is understood to mean any plant having the possibility of integrating a gene at the nuclear level in a manner which is stable and transmissible to its direct progeny.

Also for the purposes of the present invention, regenerable is understood to mean any plant having the capacity to produce neoformed plants (neoformation or micropropagation).

In a nonlimiting manner, the following plants can be subjected to transformation in accordance with the invention:

tobacco, rape, sunflower, soya bean, tomato, potato, melon, carrot, pepper, chicory, clover, lupin, bean, pea, maize, wheat, rye, oat, barley, rice, millet, citrus, cotton.

The plants, from which the unedited mitochondrial genes are obtained, are selected such that the changes in nucleotides (process called editing) between the unedited sequence and the edited sequence are substantial: at least 8 modified codons, and preferably at least 10 modified codons.

Preferably, the unedited mitochondrial genes are obtained, in a nonlimiting manner, from wheat, tobacco, petunia or potato.

Yeast presequences are in particular functional in the import of proteins into the mitochondrion in plants.

In accordance with the invention, the plant from which the said unedited mitochondrial gene is obtained and the plant which incorporated the transgene may be identical or different.

Surprisingly, the plants transformed by such a sequence have, in at least 50% of them, a male-sterile phenotype, while having no other disruptions as regards the development of the plant.

Also surprisingly, such transgenic plants make it possible to control, in a reliable and reproducible manner, the natural process of MCS, especially by avoiding self-pollination, without introducing new, artificial and destructive functions into the latter, as is the case especially in the systems described by Mariani et al. (RNAse system) or by WORRALL D. et al. (callase system).

The subject of the present invention is also a hybrid nucleic acid sequence, comprising at least the coding region of an unedited mitochondrial gene from higher plants, with which is associated a sequence capable of transferring the protein expressed by the said coding region to the mitochondrion, characterized in that:

the coding regions of the unedited mitochondrial genes are chosen from among the genes encoding a protein of the ATP synthase complex which are chosen from among the wheat ATP9 gene fragment, of the following formula I:

```
                                    (SEQ ID NO: 7)
ATG TTA GAA GGT GCT AAA TCA ATA GGT GCC GGA GCT

GCT ACA ATT GCT TTA GCC GGA GCT GCT GTC GGT ATT

GGA AAC GTC CTC AGT TCT TTG ATT CAT TCC GTG GCG

CGA AAT CCA TCA TTG GCT AAA CAA TCA TTT GGT TAT

GCC ATT TTG GGC TTT GCT CTC ACC GAA GCT ATT GCA

TTG TTT GCC CCA ATG ATG GCC TTT CTG ATC TCA TTC

GTT TTC CGA TCG CAT AAA AAG TCA TGA
``` or the ATP6 gene, or from among the genes encoding a protein of the respiratory chain, which are chosen from among the genes for subunits 1 to 7 of NAD dehydrogenase, for apocytochrome b and for subunits I, II or III of cytochrome oxidase, and the nucleic sequence capable of transferring the said expressed protein to the mitochondrion is selected from the group consisting of the fragments encoding yeast tryptophanyl tRNA synthetase, the f subunit of Nicotiana plumbaginifolia ATPase, the maize ATP/ADP translocator and a 303 base pair EcoRI/KpnI fragment including codons 1 to 62 of subunit IV of yeast cytochrome oxidase, which hybrid sequence is capable of modifying male fertility in plants having incorporated it.

According to an advantageous embodiment of the said hybrid nucleic acid sequence, it comprises the coding region of formula I of the gene encoding the unedited form of wheat ATP9, with which is associated as transfer sequence, codons 1 to 62 of the presequence of subunit IV of the yeast cytochrome oxidase (cox IV) (SEQ ID No. 1).

According to another advantageous embodiment of the said hybrid nucleic acid sequence, it comprises the fragment of the region encoding the unedited form of wheat ATP6, of formula II above, with which is associated as transfer sequence, codons 1 to 62 of the presequence of subunit IV of yeast cytochrome oxidase (cox IV) (SEQ ID No. 3).

According to another advantageous embodiment of the said hybrid nucleic acid sequence, it comprises the fragment of the region encoding the unedited form of cox II of formula III above, with which is associated as transfer sequence, codons 1 to 62 of the presequence of subunit IV of yeast cytochrome oxidase (cox IV) (SEQ ID No. 5).

The subject of the present invention is also a plasmid, characterized in that it includes a hybrid nucleic acid sequence in accordance with the invention, associated with a promoter chosen from the promoters which are constitutively expressed and the promoters which are expressed in the anthers and with a suitable terminator.

According to an advantageous embodiment of the said plasmid, it comprises the 35S promoter and the terminator of the CaMV VI gene. According to another advantageous embodiment of the said plasmid, it comprises in addition at least one marker gene, especially, and in a nonlimiting manner, a gene for resistance to an antibiotic, and preferably the gene for resistance to hygromycin.

In accordance with the invention, the transgenic plants, as defined above, are capable of being obtained by means of a process for producing transgenic plants which comprises, for the transformation of the selective higher plant, the introduction of at least one copy of the hybrid nucleic sequence as defined above, into a recipient plant, by means of a plasmid containing the said sequence, as defined above.

Such a transformation can advantageously be obtained by one of the following methods: protoplast transformation, agrotransformation, microinjection, biolistic.

The subject of the present invention is also a process for inhibiting the production of pollen in higher plants, characterized in that it comprises the following steps:

(a) inserting a hybrid nucleic acid sequence, as defined above, into the selected plants, by any appropriate means;

(b) regenerating and culturing the transgenic plants obtained in (a); and (c) measuring the production and the viability of the pollen (test of germination in particular).

Also surprisingly, the male function of the said transgenic male-sterile plants, in accordance with the invention, can be restored by crossing the said transgenic male-sterile plants with transgenic plants comprising in their nuclei a so-called antisense hybrid nucleic acid sequence, that is to say including at least the same coding region of unedited plant mitochrondrial gene as that included in the said transgenic male-sterile plants, in the reverse direction.

The subject of the present invention is also a process for restoring male-fertile plants, from transgenic male-sterile plants, in accordance with the invention, characterized in that it comprises the following steps:

(1) transforming the selected higher plant by introducing at least one copy of the hybrid nucleic sequence as defined above, into a recipient plant, by means of a plasmid containing the said sequence, in order to obtain transgenic male-sterile plants (TMSP); transforming the same higher plant as in (1), by introducing at least one copy of an antisense hybrid nucleic sequence, including at least the same coding region of the unedited plant mitochondrial gene as that included in the said transgenic male-sterile plants obtained in (1), into a recipient plant, by means of a plasmid containing the said sequence, in order to obtain transgenic male-fertile plants (TMFP); crossing the transgenic male-sterile plants obtained in (1) and the male-fertile plants obtained in (2), in order to obtain vigorous hybrids whose male fertility has been restored and which have preselected characteristics. The subject of the present invention is also plasmids including an antisense hybrid sequence, as defined above, associated with a promoter chosen from among the constitutive promoters and the promoters specific for the anthers and also associated with a suitable terminator.

In addition to the preceding arrangements, the invention also comprises other arrangements, which will emerge from the description below, which refers to exemplary embodiments of the process which is the subject of the present invention.

It should be understood, however, that these examples are given solely by way of illustration of the subject of the invention and do not in any manner constitute a limitation thereto.

EXAMPLE 1
Construction of a Chimeric Gene in Accordance with the Invention Cox IV-ATP9 (SEQ ID No. 1)

The sequences encoding ATP9 are obtained from a cDNA corresponding to the edited and unedited forms of wheat mitochondrial mRNA.

ATP9 is fused with a 303 base pair EcoRI/KpnI fragment from a plasmid called 19.4 (MAARSE et al., EMBO J., 1984, 3, 2831–2837), including codons 1 to 62 of subunit IV (cox IV) of yeast cytochrome oxidase.

Figure 3:
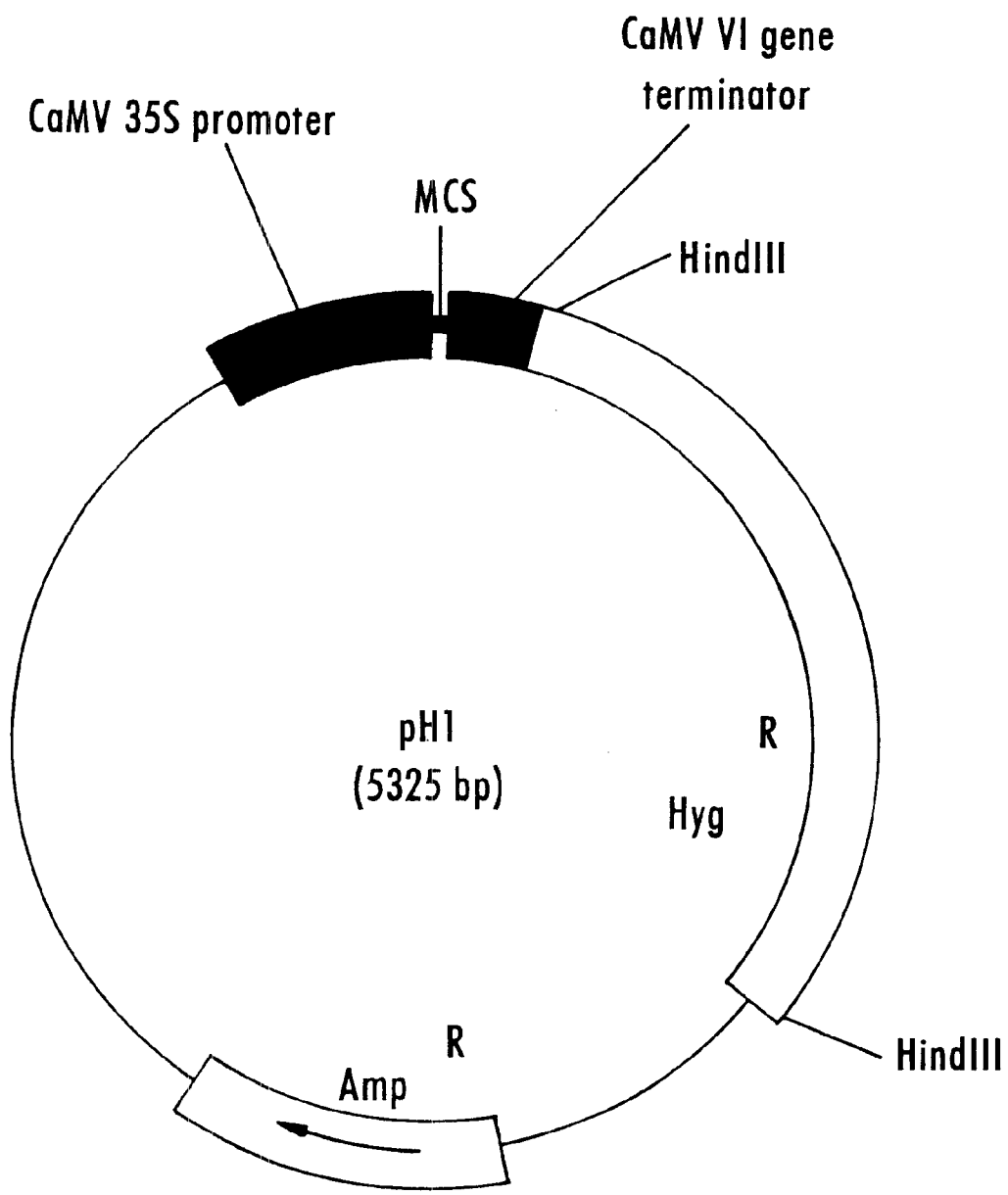
FIG. 3 depicts plasmid pH1.
Figure 4:
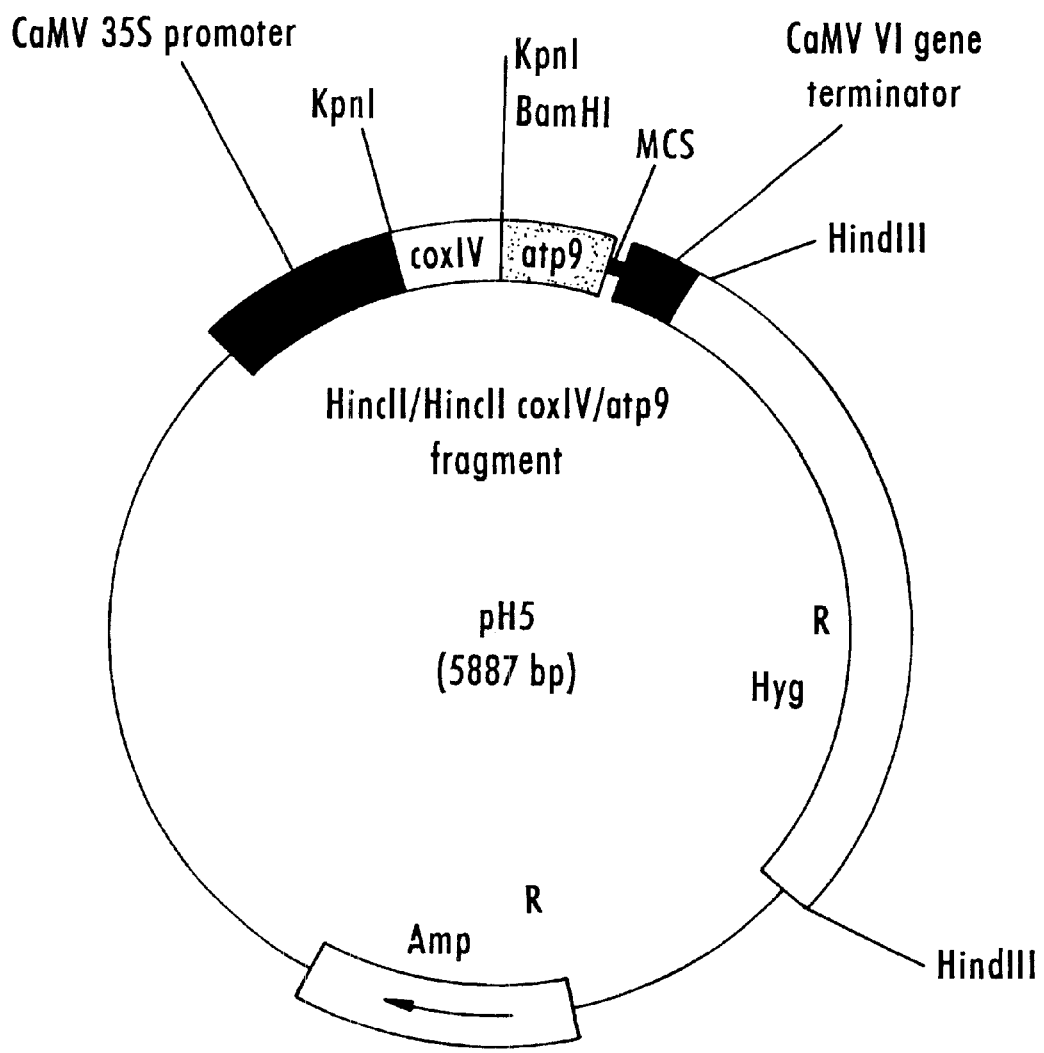
FIG. 4 depicts plasmid pH5.
Figure 5:
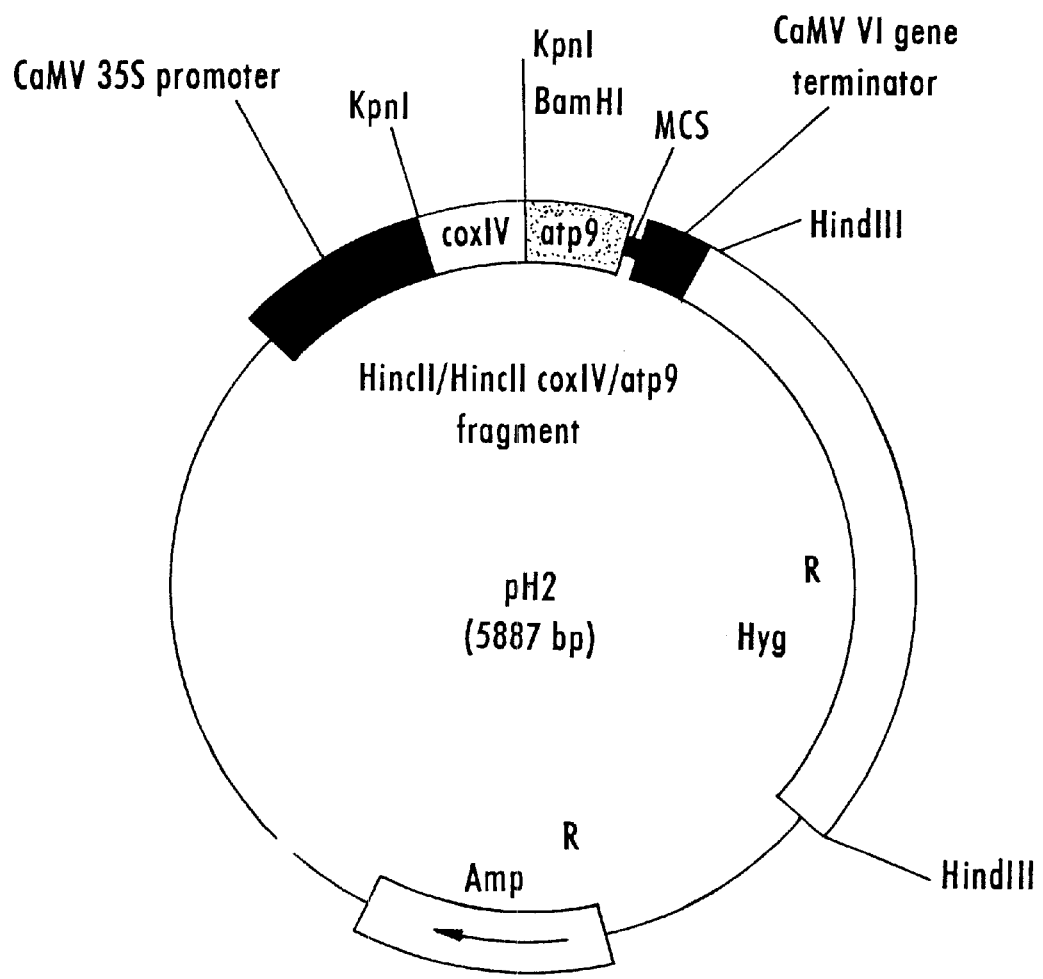
FIG. 5 depicts plasmid pH2.
Figure 6:
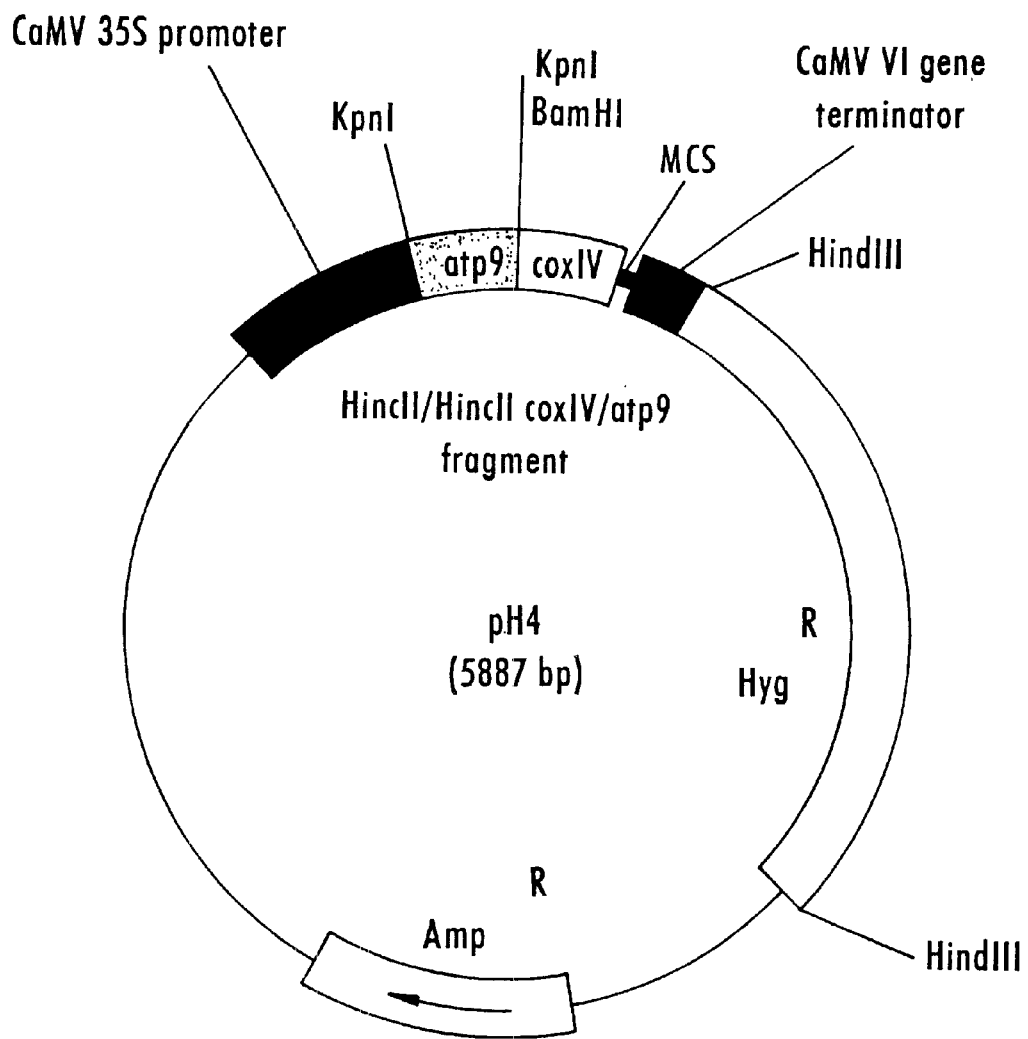
FIG. 6 depicts plasmid pH4.

The resulting fragment, obtained after digestion with the enzyme HincII is ligated at the level of the SmaI restriction site of the plasmid pDH51 (PIETRZAK et al., 1986, Nucleic Acids Res., 14:5857–5858). The hygromycin resistance gene is inserted at the level of the Hind III site of the plasmid pDH51, of the plasmid pEA903 (edited form of ATP9, FIG. 1) and of the plasmid pEA904 (unedited form of ATP9, FIG. 2) giving rise to the plasmids pH1 (FIG. 3), pH5 (FIG. 4) and pH2 (FIG. 5) respectively. The plasmid pH4 (FIG. 6) consists of the plasmid pEA904 in which the coding part cox IV/ATP9 is placed in reverse orientation compared with the plasmid pH2.

The unedited cox IV-ATP9 and edited cox IV-ATP9 sequences are represented in FIGS. 12 and 13.

All these genes are under the control of the CaMV 35S promoter and of the CaMV VI gene terminator.

The sequences in accordance with the invention can be specifically amplified by means of the following oligonucleotide primers:

(a) 5'-CACTACGTCAATCTATAAG-3' (SEQ ID No:10), extending from codon 3 to codon 9 of the presequence of subunit IV of yeast cytochrome oxidase and 5'-TATGCTCAACACATGAGCG-3' (SEQ ID No:11), localized at the level of the CaMV VI gene terminator (45 base pairs upstream of the polyadenylation signal). The ATP9 mRNA in wheat undergoes C—U nucleotide changes (process called editing), at the level of 8 codons. The consequence of these modifications is the change of 5 amino acids in the corresponding protein (edited protein) and the loss, compared with the deduced sequence of the gene, of 6 residues from the C-terminal region, a loss which is caused by the creation of a stop codon.

The unedited protein is more hydrophilic with 6 additional residues at the C-terminal level; furthermore, this selected unedited form of ATP9 constitutes a particularly advantageous model of modified protein because it constitutes one element of the ATP synthase proton channel and, consequently, it is essential for the function of this complex; this fragment is also advantageous because of the small size of the coding sequence, which facilitates handling, and the fact that ATP9 may have a nuclear or mitochondrial localization.

EXAMPLE 2
Production of Transgenic Male-sterile Plants

Both the plasmid constructs in accordance with the invention (see Example 1, plasmid pH2) and the control constructs (plasmid pH1) and the constructs corresponding to the edited form of ATP9 (plasmid pH5) are used for the transformation of protoplasts of a *Nicotiana tabacum* cv. Petit Havana line, called SR1.

Transformation of the Protoplasts

The protoplasts used for the transformation are isolated from the leaves of Nicotiana tabacum SR1 plants, cultivated under axenic conditions and one month old. The young leaves are removed, the central vein eliminated and the leaves are cut into thin slices. The fragments are then incubated in the dark at 26° C., overnight, in an enzymatic solution consisting of K3 medium (NAGY and MALIGA, 1976) supplemented with R10 Onozuka cellulase (1.2%), R10 Onozuka macerozyme (0.4%) and Fluka driselase (0.1%) (pH 5.6). Before theharvest, the enzymatic solution is diluted with a 0.6M sucrose solution, 0.1% (w/v) MES (pH 5.6) in the respective proportions 2v/1v. The protoplasts are separated from the undigested tissues by filtration through a 100 μm sieve. The suspension is covered with a W5 solution (MENCZEL et al., Theor. Appl. Genetics, 1981, 59:191–195) being careful not to mix the liquid phases. After centrifuging at 600 rpm for 10 min, the protoplasts are assembled in the form of a band at the interface between the W5 solution and the enzymatic solution. They are carefully collected and washed twice with the W5 solution in order to remove traces of enzymes. The protoplasts are placed in a cold chamber at 4–6° C. for 1–2 hours. After another centrifugation at 750 rpm for 5 min, they are resuspended in a mannitol/magnesium solution (0.5M Merck mannitol; 1.5 mM Prolabo $MgCl_2$ $6H_2O$, 0.1% Sigma MES, pH 5.6) and their concentration is adjusted to $1.6 \times 10^6$ protoplasts/ml. The protoplasts are subjected to a heat shock at 45° C. for 5 minutes.

After returning to room temperature, 300 µl of protoplast suspension ($5 \times 10^5$ protoplasts) are distributed in a 12 ml conical tube. Next, 20 µg of plasmid pH2 (or of plasmid pH4), depending on the transgenic plant which it is desired to obtain, 300 µl of a solution of PEG 4000>40% (w/v) Merck PEG 4000; 0.4M Merck mannitol; Merck $Ca(NO_3)_2$ $4H_2O$; pH 8 (solution sterilized by filtration on 0.45 µm) and 60 µg of calf thymus DNA as carrier DNA, are added to the protoplast suspension. The mixture is incubated at room temperature for 25–30 minutes and gently stirred from time to time. The transformation suspension is then gradually diluted by adding, in small portions, 10 ml of W5 over a period of 10 minutes. The protoplasts are recovered by centrifugation and taken up in 1 ml of K3 medium.

Culture of the Protoplasts and Regeneration of Plants

The protoplasts are cultured in an amount of $5 \times 10^4$ protoplasts/ml, in 3 ml of a mixture of K3 and H medium (KAO and MICHAYLUK, 1975) in a 1:1 (v/v) proportion, solidified with agarose (0.8%). The resulting colonies are gradually cultured in the presence of hygromycin selection agent at 20 mg/l, in A50m medium (A medium containing 50 g/l mannitol) (CABOCHE, 1980) for the first month, and then on A30m medium (the A medium containing 30 g/l mannitol) for the second month, and finally on A-m medium (A medium without mannitol), medium containing 40 mg/ml of hygromycin, during the third month. For the regeneration, the calli are transferred onto the AR medium. The AR medium is the A medium containing only 20 g/l sucrose as carbohydrate source and 0.25 mg/l BAP as growth hormone.

The plantlets derived from the calli are cultured on T medium (NITCH and NITCH, 1969). The MSoo medium is used for maintaining the plants.

EXAMPLE 3
Phenotypic Analysis of the Transgenic Plants Obtained

The sizes of the 14-week old plants obtained in accordance with Example 2 are specified in Table I below

TABLE I

| | | Fertility of the plant[1] | | | | | |
|---|---|---|---|---|---|---|---|
| Lines | Number of plants tested | F (%) | F/S (%) | S (%) | Groove (cm) | Number of nodes | Seeds[2] (mg) |
| SR1 | 1 | 100 | 0 | 0 | 87.0 | 24 | 109 ± 36 |
| H1 | 3 | 100 | 0 | 0 | 120 ± 6 | 19 ± 1 | 108 ± 14 |
| H2 | 16 | 50 | — | — | — | — | 100 ± 32 |
| | | — | 19 | — | 103 ± 26 | 19 ± 2 | 25 ± 17 |
| | | — | — | 31 | — | — | 0 |
| H5 | 9 | 100 | 0 | 0 | 92 ± 23 | 23 ± 5 | 94 ± 28 |

[1]F = fertile, F/S = semifertile, S = malesterile
[2]mean value of production of seed per capsule after selfpollination
H1 line = transgenic plants obtained with the plasmid pH1,
H2 line = transgenic plants obtained with the plasmid pH2,
H5 line = transgenic plants obtained with the plasmid pH5,
Control line SR1 (nontransformed plant).

The size of the plants is not significantly different from that of the nontransformed SR1 lines. The mean number of nodes is similar in the three different transgenic lines (19 to 24 nodes per plant).

Apparently, there is no change in the function of the vegetative meristems in the differentiation of the nodes and of the leaves of the transgenic plants.

Figure 2:
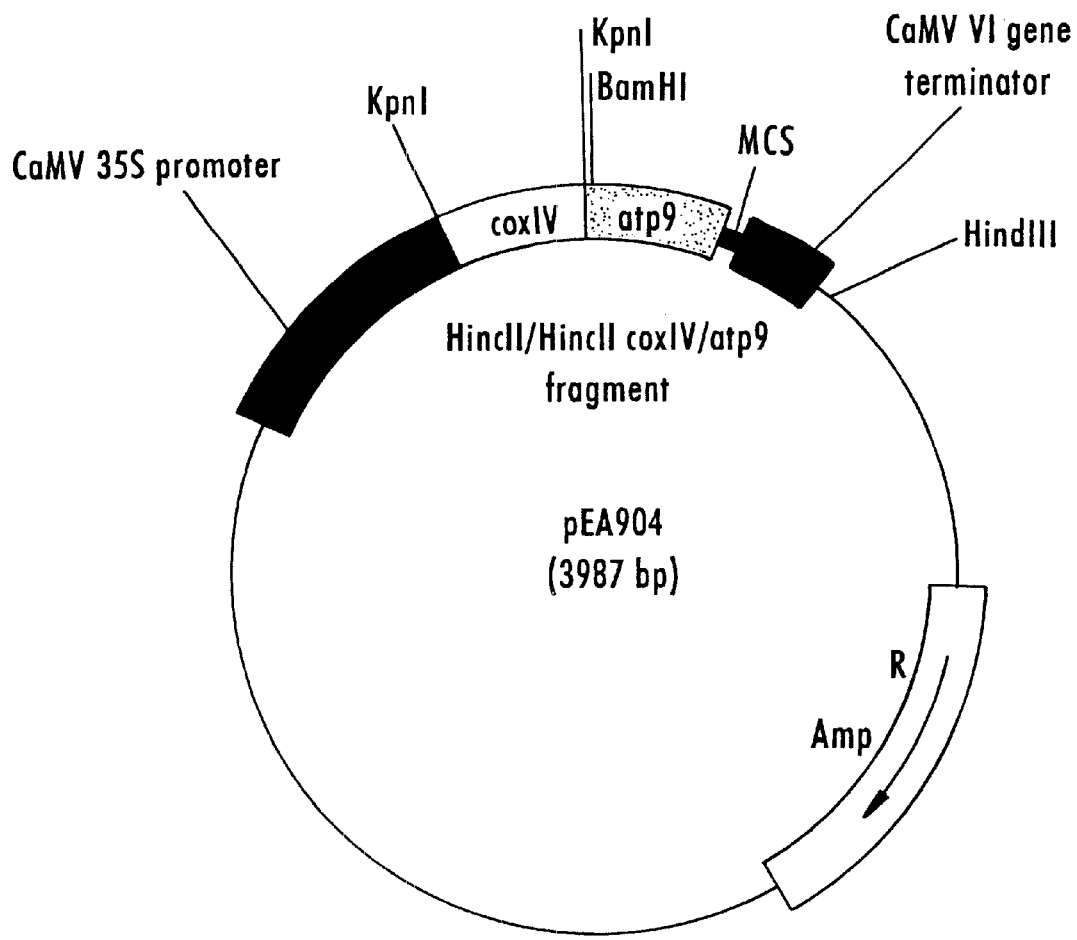
FIG. 2 depicts plasmid pEA904.

Flowering in the H1, H2 and H5 lines is induced to 14 weeks after transplantation. The flowers from the transgenic plants are similar in shape and in colour to those of the SR1 flowers (red-pink petals and anthers in each flower). The male-sterile plants have white anthers containing few or no pollen grains (FIGS. 7A1 and 7B), whereas the fertile plants have yellow-white anthers with normal pollen grains (FIGS. 7A2 and 7C). There is no difference in the shape and in the colour of the pistil between the male-sterile and male-fertile plants.

EXAMPLE 4
Analysis of the Fertility of the Transgenic Plants

The transformants H1 and H5 produce fertile plants, whereas the transformants H2 have fertility, semi-fertility or sterility characteristics which are defined on the basis of germination of the pollen or by the reaction with fluorescein diacetate.

In the transgenic fertile plants, the viability of the pollen is between 31 and 75%, close to the values found in the SR1 control line; in the semifertile plants, the viability of the pollen is about 10 to 20%; in the male-sterile plants, the viability is generally less than 2%.

The fertility of the plants is also determined by the production of seeds after self-pollination or backcrossing. The results are also illustrated in Table I above.

The H1 and H5 lines have a mean seed production of 100 mg/capsule, comparable with that of the SR1 control lines (110 mg/capsule). The H2 lines which correspond to sterile plants produce no seed, the semifertile plants produce between 12 and 50 mg/capsule, the fertile plants produce on average 100 mg/capsule. These values correlate well with the pollen viability.

The female fertility characteristic, for the sterile and semifertile plants, is determined by backcrossing with the SR1 lines as male parent.

All the male-sterile plants are fertile females and produce a normal quantity of viable seeds (63 to 92 mg/capsule), with a seed viability value greater than 77%. Thus, the sterile or semifertile character in 50% of the H2 lines is due to the absence or to the very low production of viable pollen.

The transmission of the transgenes is analysed through the genetic segregation of the hygromycin phosphotransferase (hpt) gene in the descendants (between 200 and 500 descendants analysed. After self-pollination (fertile and/or semifertile plants), the resistance to hygromycin is transmitted in most of the cases as a mendelian (mono- or digenic) character.

After backcrossing with the SR1 parent (sterile plant), four of the five male-sterile plants inherit the character for hygromycin resistance as a digenic mendelian character, this expressing two active loci.

These analyses show that the sterile plants are only affected in relation to the production of pollen, since they are fertile females and produce a quantity of seeds per fruit (100 to 150 mg) comparable or even greater than that of the controls.

EXAMPLE 5

Molecular Analysis of the Transformants

In order to demonstrate the presence and the transcription of the ATP9 transgene, the analysis of the transcription products is performed by Southern and Northern type hybridization. The total DNA is isolated from the (sterile, semifertile and fertile) H2 lines and the H5 lines. Moreover, the chimeric gene is analysed by PCR amplification.

Methods used

The total DNA is isolated from 10 g of leaf tissue essentially as described in SAGHAL-MAROOF M. A. et al., 1984. Proc. Natl. Acad. Sci. USA, 81, 8014–8018. 1 $\mu$g of DNA is amplified in a final volume of 100 $\mu$l, using 0.5 unit of Taq polymerase, 0.18 mM dNTPs and 100 pmol of each of the primers. The primers used re those specified in Example 1. The use of these primers excludes the amplification of the endogenous ATP9 (see FIG. 8C).

The denaturation step is performed at 95° C. for 1 min, the hybridization step is performed for 2 min at 52° C. and the polymerization step is performed for 1 min at 72° C.

25 cycles are performed, the samples are subjected to electrophoresis on a 1.5% agarose gel and transferred onto a Hybond-N$^+$ membrane (Amersham), as described in SAGHAL-MAROOF M. A. al. (reference cited). The filters are prehybridized at 42° C. in 50% deionized formamide, 5×SSC, 8×Denhardt and 0.5% SDS. The filters are hybridized with the 300 base pair coding sequence of ATP9, a 32P-labelled EcoRI/HindIII fragment.

Figure 8A:
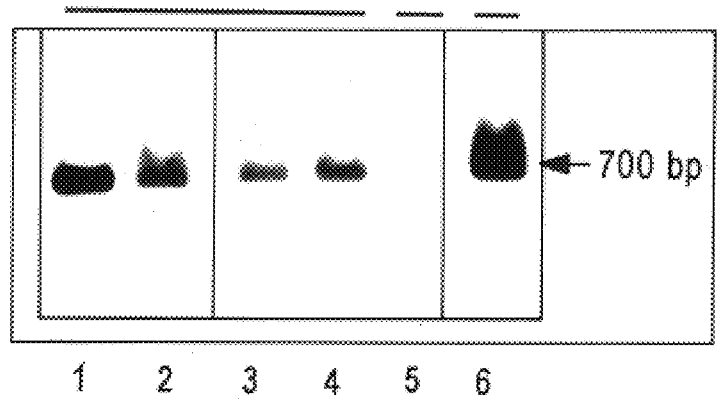
FIGS. 8A–8C depict analysis of transgenes (8C) by PCR (8A) and analysis of the poly A+ transcripts of transgenic plants by Northern hybridization (8B).

A band (corresponding to a product comprising 700 base pairs) is observed in most of the H2 and H5 lines as expected. FIG. 8A shows the results obtained with the H2.2 and H2.16 DNA derived from male-sterile plants (lanes 1 and 2) and with fertile plants (H5.6 and H5.15 DNA, lanes 3 and 4). The DNA derived from nontransformed plants SR1 gives no signal (lane 5).

The total RNA from the SR1, H2 and H5 lines is extracted, from the leaves, as follows: 5 g of leaves are cryo ground; then a first extraction is performed using the frozen powder, with 5 ml of a phenol; chloroform; isoamyl alcohol mixture (25:24:1; v:v:v) and 5 ml of TNES+DTT (0.1 M NaCl, 10 mM Tris-HCl pH 7.5, 1 mM EDTA, 0.1% SDS and 2 mM dithiothreitol); a second extraction is then performed, using the aqueous phase, twice with an equal volume of chloroform and isoamyl alcohol (24:1; v:v) and the RNA is precipitated with an equal volume of 4 M lithium chloride at 0° C. overnight.

The RNAs are dissolved in DEPC-treated water. The RNA concentration is measured by the optical density (OD) at 260 nm. The poly(A)$^+$ RNAs are purified by oligo(dT)-cellulose affinity chromatography. 20 $\mu$g of total RNA and 1 $\mu$g of poly(A)$^+$ RNA are subjected to electrophoresis on 1.5% agarose gel, formaldehyde/formamide buffer, and then transferred onto Hybond-N.sup.+ nylon membranes. The hybridizations with the ATP9 probe are performed as described above.

Figure 8B:
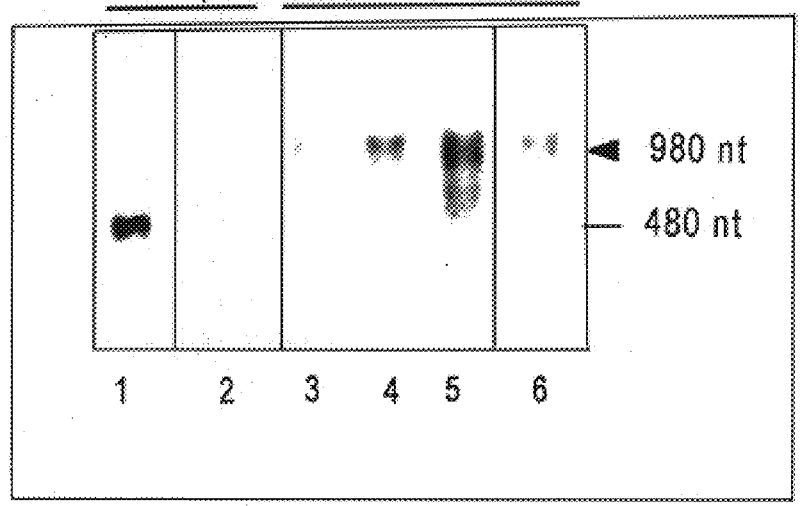
Figure 8C:
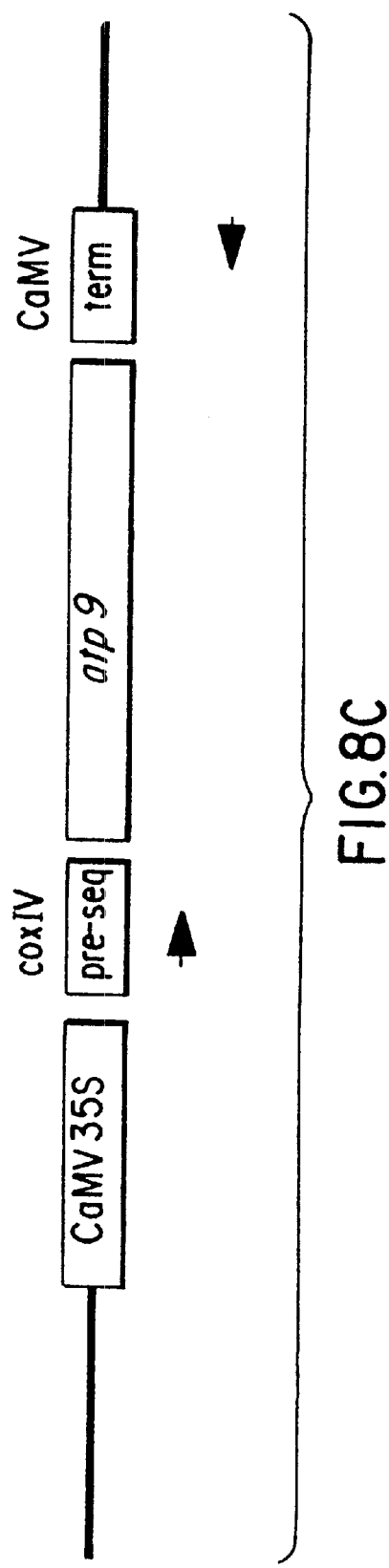

A 0.48 kb band is obtained with the SR1 control lines (FIG. 8B, lane 1). This band is present in all the lines and corresponds to the mitochondrial endogenous mRNA.

An additional transcript, corresponding to a 0.98 kb band is present only in the transformed plants. As illustrated in FIG. 8B, these molecules can be separated from the endogenous mRNA by oligo(dT)-cellulose chromatography, confirming its cytoplasmic origin.

FIG. 8B, (lanes 3 and 4), shows the results obtained with the male-sterile plants H2.2 and H2.16 and with the fertile plants H5.6 and H5.15, (lanes 5 and 6). The 0.98 kb transcript is absent from the nontransformed controls (lane 2).

In parallel, by the PCR technique for cDNA, it is possible to obtain transcripts derived from the transgene by virtue of the sequences added during the in vitro manipulation such as the presequence regions obtained from the yeast (cox IV) and the CaMV termination region. Furthermore, only the 0.98 kb transcript hybridizes with a probe obtained from the cox. IV sequence fused with ATP9.

EXAMPLE 6

Analysis of the Production of the Chimeric Protein

In order to understand if the transgenes affect the expression of the endogenous mitochondrial ATP9 gene, the total RNA from the transformed plants H2 and H5 as well as from the control plants was hybridized with a specific mitochondrial probe.

Figure 9:
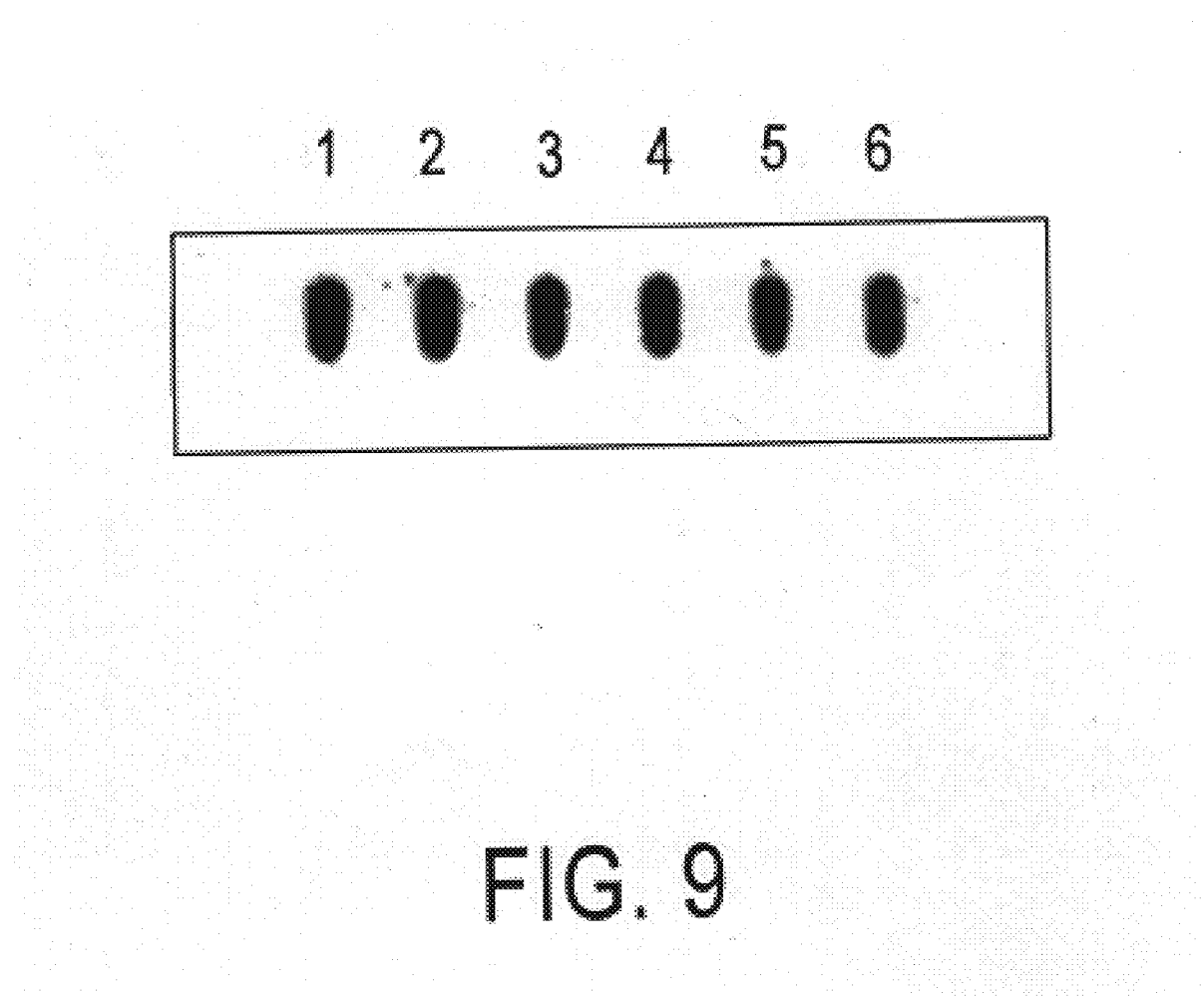
FIG. 9 depicts analysis of total RNA from transformed plants H2 and H5 and from control plants.

As shown in FIG. 9, no substantial difference is observed when the transgene is edited or unedited and the labelling is similar to that of the control.

The production of the transgenic protein is analysed by immunoblotting of the mitochondrial and cytosolic extracts. Antibodies directed against fragments 21 to 54 of the presequence part of yeast cox IV, which are part of the transgene, are obtained in rabbits.

The procedure is carried out as follows: a XbaI/KpnI fragment containing codons 21 to 54 of yeast cox IV is isolated from the abovementioned plasmid 19.4.

Figure 10:
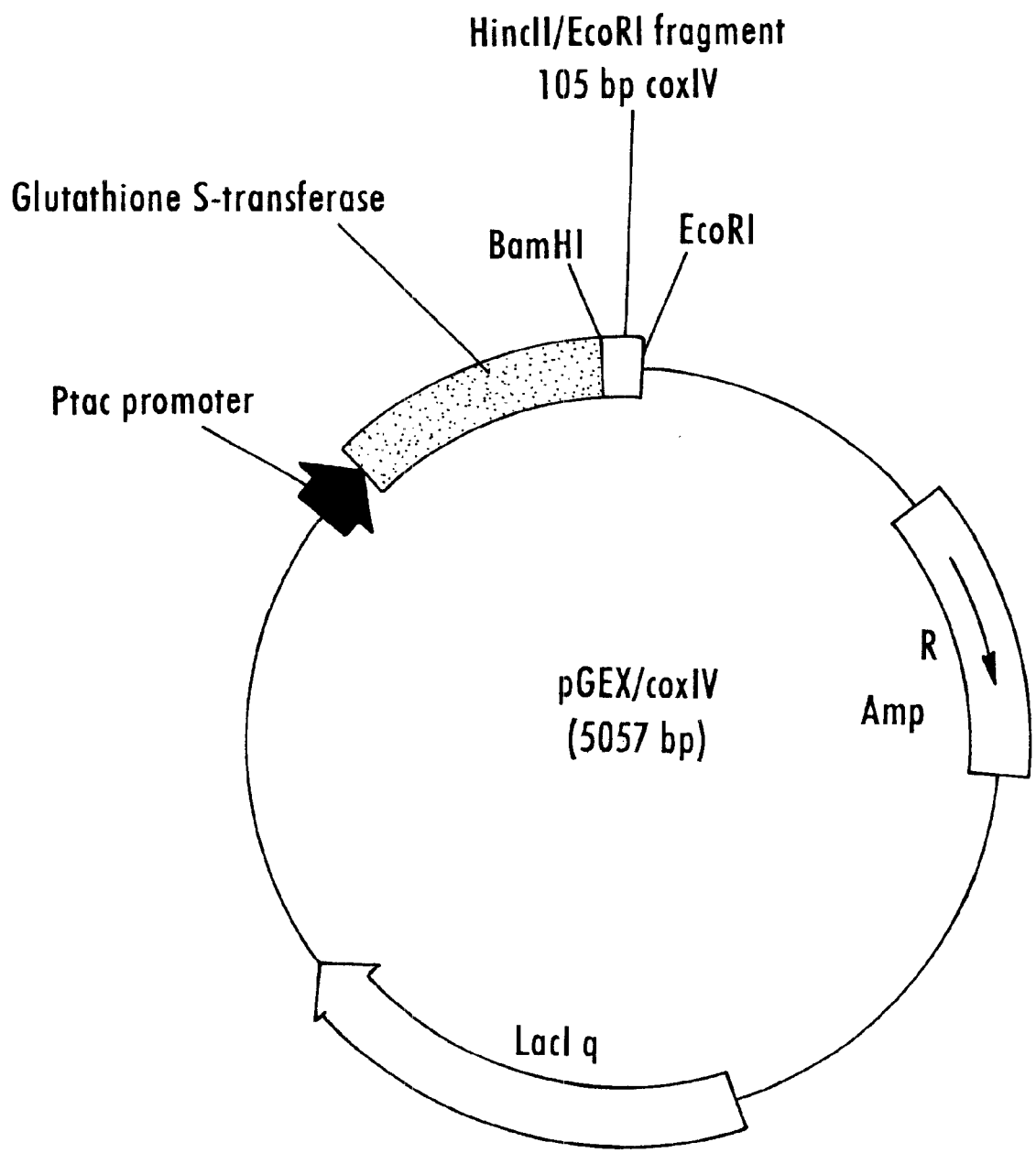
FIG. 10 depicts plasmid pGEX/coxIV.

This fragment is ligated to the plasmid pGEX-A (FIG. 10) in phase with the coding sequence of glutathione S-transferase, under the control of the β-galactosidase promoter.

The fusion protein is induced after transformation of E. coli DH5A cells by IPTG. These cells produce about 80 mg of protein per liter of culture.

The fused protein is purified from an E. coli extract by affinity chromatography on a glutathione agarose column. The protein eluted by glutathione is obtained with a purity level of the order of 95%. The fusion protein is used as antigen to produce anti-cox IV antibodies in rabbits.

Greenhouse plant leaves are used for cell fractionation. 100 $\mu$g of cytosolic and mitochondrial proteins are fractionated by urea/SDS-PAGE. The immunoreaction is performed using an anti-cox IV antiserum diluted 1/500th according to the DARLEY-USMAR et al. method >1987, Mitochondria,

*a practical approach,* eds DARLEY-USMAR, (IRL Press Ltd.) pp. 113–152!. The proteins from transgenic plants carrying the male-sterile phenotype are revealed by peroxidase-conjugated anti-rabbit IgG antibodies.

Figure 11:
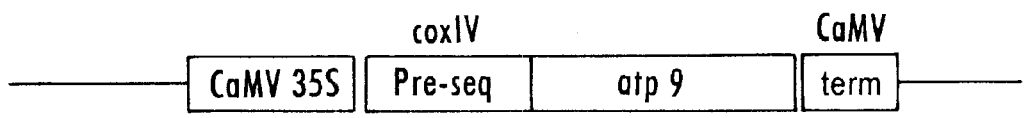
FIG. 11 depicts the intracellular localization of transgenic proteins by immunoblotting.

No signal is observed either with the mitochondrial fraction (FIG. 11B, lane 1), or with the cytosolic fraction from the nontransformed SR1 line.

The mitochondrial fraction of the H2.2 male-sterile and H5.15 fertile plants (FIG. 11B, lanes 2 and 4 respectively) show a 12 kDa band corresponding to the expected size for the protein (see FIG. 11A, which specifies the structure of the 15 kDa precursor and the 12 kDa imported protein).

The cytosolic proteins from these lines (FIG. 11B, lanes 3 and 5) show two bands, one at 15 kDa, the expected size for the chimeric precursor polypeptide, and the other at 14 kDa. The nature of this latter polypeptide remains to be determined; it is probably a degradation product of the 15 kDa precursor.

The protein associated with the mitochondrial fraction of the H5.15 line (FIG. 11, lane 4) migrates roughly to the same position as the mitochondrial protein H2.2, but slightly downstream. This difference is due to the fact that the chimeric genes differ in the position of their stop codon. Indeed, as already specified above, the edited protein has 6 residues less than the unedited protein due to the generation of a stop codon during the editing of the RNA.

EXAMPLE 7

Study of the Respiration of the Mitochondria from the Transgenic Plants

The effect of the transgene at the subcellular level should result in a dysfunction of the respiratory function of the mitochondrion. Analysis of the respiration of the nonchlorophyllian plants of the transgenic plants was performed.

The determination of the respiration rates of the nonchlorophyllian organs (roots), in the presence or in the absence of decouplers, is carried out by analysing the consumption of oxygen by means of a Clark electrode. More detailed studies were performed on mitochondria purified by differential centrifugation and on a Ficoll gradient. The effect of decouplers on respiration and the ADP/O ratios were determined on mitochondria derived from male-sterile lines and compared with the transformed or wild-type control plants.

These different measurements show that the mitochondrial function is reduced in the male-sterile plants compared with the nontransformed or transformed control with the plasmid pH5. This situation is similar to that encountered in the natural male-sterile plants.

It stems from the above that the expression in the transgenic tobacco plants of a DNA sequence encoding unedited wheat mitochondrial ATP9 has no effect on most of the phenotypic characters of the transformed plants, except for the appearance of male sterility.

Indeed, the size, the growth rate, the number of nodes, the shape and the size of the leaves and of the flowers are similar in the transgenic plants and in the control plants. However, significant effects are observed in the male reproductive organs when the wheat ATP9 sequence, in its unedited form, is expressed in tobacco plants.

Indeed, the transformation experiments performed with the plasmid pH2 lead to the production of many plants (50%) modified in relation to their fertility. Approximately 19% are semifertile and 31% are completely sterile.

All the semifertile and sterile H2 lines express the transgene in the polyadenylated mRNA form. The fertile H2 lines do not have the 0.98 kb transcript, even when the transgene is detected after PCR amplification, thereby indicating that the transgene is inactive in this latter case.

Some results also show, unexpectedly, that the male-sterile phenotype is correlated only with the presence of unedited ATP9 sequence whereas the transformants obtained with the edited ATP9 form are all fertile.

In all cases, the sterile plants are only male-sterile plants and can be pollenated with a foreign pollen, thereby reflecting a normal female fertility.

EXAMPLE 8

Production of Transgenic Plants Having an Antisense Hybrid Sequence in Accordance with the Invention The procedure is carried out as in Example 2, the transformation of protoplasts being however performed by means of the plasmids pH4.

By crossing these male-fertile plants with the male-sterile transgenic plants in accordance with the invention, noninbred male-fertile hybrids are obtained.

EXAMPLE 9

Construction of a Chimeric Gene in Accordance with the Invention Cox IV-ATP6 (SEQ ID No. 3)

The sequences encoding ATP6 are obtained from a cDNA corresponding to the edited and unedited forms of wheat mitochondrial mRNA.

The unedited ATP6 fragment selected has the sequence of formula II defined above and is fused with the yeast transfer sequence cox IV as defined above.

The resulting fragment is similar to that obtained in Example 1.

The ATP6 mRNA in wheat undergoes nucleotide changes (editing) at the level of 12 codons. The consequence of the modifications is the change of 11 amino acids and the loss, compared with the deduced sequence of the gene, of 7 residues, from the C-terminal region, a loss caused by the creation of a stop codon.

EXAMPLE 10

Construction of a Chimeric Gene in Accordance with the Invention cox IV-cox II (SEQ ID No.5)

The sequences encoding cox II are obtained from a cDNA corresponding to the edited and unedited forms of wheat mitochondrial mRNA.

The fragment of the unedited cox II gene has the sequence of formula III defined above and is fused with the yeast transfer sequence cox IV as defined above.

The resulting fragment is similar to that obtained in Example 1.

The mRNA in wheat undergoes nucleotide changes (editing) in 16 codons. The consequence of the modifications is the change of 16 amino acids compared with the deduced sequence of the cox II gene.

As evident from the above, the invention is riot in the least limited to the implementations, embodiments and applications which have just been described more explicitly; on the contrary, it embraces all the variants which may occur to a specialist in this field without departing from the framework or the scope of the present invention.

What is claimed is:

1. Transgenic plants having in their nuclei an expressible hybrid sequence comprising at least one coding region of an unedited mitochondrial gene from higher plants and a sequence capable of transferring the protein expressed by the said coding region to the mitochondrion, wherein:

the coding regions of the unedited mitochondrial genes are selected from the group consisting of the genes encoding a protein of the ATP synthase complex which are selected from the group consisting of the wheat ATP9 gene fragment of SEQ ID No:7 in unedited form and ligated to a mitochondrial transporter sequence, wherein the hybrid nucleic acid sequence comprising the ATP 9 gene, when transformed into a recipient plant, causes male sterility, and the wheat ATP6 gene in unedited form and ligated to a mitochondrial transporter sequence, wherein the hybrid nucleic acid sequence comprising the ATP 6 gene, when transformed into a recipient plant, causes male sterility, and the sequence capable of transferring the said expressed protein to the mitochondrion is selected from the group consisting of the fragments encoding yeast tryptophanyl tRNA synthetase, the β subunit of *Nicotiana plumbaginifolia* ATPase, the maize ATP/ADP translocator and a 303 base pair EcoRI/KpnI fragment comprising codons 1 to 62 of subunit IV of yeast cytochrome oxidase, which hybrid sequence is capable of modifying male fertility in plants having incorporated the said transgene while not modifying the other phenotypic characteristics of the said plants.

2. Transgenic plants according to claim 1, wherein said hybrid nucleic acid sequence comprises the region of the gene encoding the unedited form of wheat ATP9, of SEQ ID NO: 7, with which is associated as transfer sequence, condons 1 to 62 of the presequence of subunit IV of the yeast cytochrome oxidase (cox IV) (SEQ ID No. 1).

3. Transgenic plants according to claim 1, wherein said hybrid nucleic acid sequence comprises the fragment of the region encoding the unedited form of wheat ATP6, of SEQ ID NO: 8, with which is associated as transfer sequence, codons 1 to 62 of the presequence of subunit IV of yeast cytochrome oxidase (cox IV) (SEQ ID No. 3).

4. Transgenic plant according to claim 1, wherein the plant having incorporated the said hybrid sequence is tobacco.

5. Transgenic plant according to claim 1, wherein the plant having incorporated the said hybrid sequence is selected from the group consisting of rape, sunflower, soya bean, tomato, potato, melon, carrot, pepper, chicory, clover, lupin, bean, pea, maize, wheat, rye, oat, barley, rice, millet, citrus and cotton.

6. Hybrid nucleic acid sequence, comprising at least the coding region of an unedited mitochondrial gene from higher plants, with which is associated a sequence capable of transferring the protein expressed by the said coding region to the mitochondrion, wherein:

the coding regions of the unedited mitochondrial genes are selected from the group consisting of the genes encoding a protein of the ATP synthase complex which are selected from the group consisting of the wheat ATP9 gene fragment of Seq ID No:7 in unedited form and ligated to a mitochondrial transporter sequence, wherein the hybrid nucleic acid sequence comprising the ATP 9 gene, when transformed into a recipient plant, causes male sterility, and the wheat ATP6 gene in unedited form and ligated to a mitochondrial transporter sequence, wherein the hybrid nucleic acid sequence comprising the ATP 6A gene, when transformed into a recipient plant, causes male sterility, and the nucleic sequence capable of transferring the said expressed protein to the mitochondrion is selected from the group consisting of the fragments encoding yeast tryptophanyl tRNA synthetase, the β subunit of *Nicotiana plumbaginifolia* ATPase, the maize ATP/ADP translocator and a 303 base pair EcoRI/KpnI fragment comprising codons 1 to 62 of subunit IV of yeast cytochrome oxidase, which hybrid sequence is capable of modifying male fertility in plants having incorporated it.

7. Hybrid nucleic acid sequence according to claim 6, comprising the region of the gene encoding the unedited form of wheat ATP9, of SEQ ID NO: 7, with which is associated as transfer sequence, codons 1 to 62 of the presequence of subunit IV of yeast cytochrome oxidase (cox I) (SEQ ID No. 1).

8. Hybrid nucleic acid sequence according to claim 6, comprising the fragment of the region encoding the unedited form of wheat ATP6 of SEQ ID NO: 8, with which is associated as transfer sequence, codons 1 to 62 of the presequence of subunit IV of yeast cytochrome oxidase (cox IV) (SEQ ID No. 3).

9. Plasmid, comprising a hybrid nucleic acid sequence according to claim 6, associated with a promoter selected from the group consisting of the promoters which are constitutively expressed and the promoters which are preferentially expressed in the anthers, and with a terminator.

10. Plasmid according to claim 9, wherein said sequence is under the control of the CaMV 35S promoter and the terminator of the CaMV VI gene.

11. Plasmid according to claim 9, comprising, in addition, at least one marker gene.

12. Transgenic plants, comprising in their nuclei an antisense hybrid nucleic acid sequence, comprising, in the reverse direction, at least the same coding region of the unedited plant mitochondrial gene as that contained in the transgenic male-sterile plants according to claim 1.

13. Plasmid, comprising a coding region of an antisense unedited plant mitochondrial gene, comprising, in the reverse direction, at least the same coding region of unedited plant mitochondrial gene as that contained in the transgenic male-sterile plants according to claim 1, associated with a promoter selected from the group consisting of promoters which are constitutively expressed and promoters which are preferentially expressed in the anthers, and with a terminator.

14. Process for producing male sterile transgenic plants comprising transforming a selected higher plant into a male sterile transgenic plant by introducing into a recipient plant at least one copy of the hybrid nucleic acid sequence that is capable of modifying male fertility in plants having it incorporated therein, wherein said hybrid nucleic acid sequence comprises at least a coding region of an unedited mitochondrial gene from a higher plant, with which is associated a sequence capable of transferring the protein expressed by the said coding region to the mitochondrion, wherein:

the coding region of the unedited mitochondrial gene is the wheat ATP6 gene in unedited form and ligated to a mitochondrial transporter sequence, wherein the hybrid nucleic acid sequence comprising the ATP 6 gene, when transformed into a recipient plant, causes male sterility; and wherein the nucleic acid sequence capable of transferring the said expressed protein to the mitochondrion is selected from the group consisting of:

the fragments encoding yeast tryptophanyl tRNA synthetase, the beta sub-unit of *Nicotiana plumbaginifolia* ATPase, the maize ATP/ADP translocator, and a 303 base pair EcoRI/KpnI fragment comprising codons 1 to 62 of sub-unit IV of yeast cytochrome oxidase.

15. Process for inhibiting the production of pollen in selected higher plants, comprising the following steps:

(a) inserting a hybrid nucleic acid sequence that is capable of modifying male fertility in plants having it incorporated therein, wherein said sequence comprises at least a coding region of an unedited mitochondrial gene from a higher plant, with which is associated a sequence capable of transferring the protein expressed by the said coding region to the mitochondrion, wherein:

the coding region of the unedited mitochondrial gene is the wheat ATP6 gene in unedited form and ligated to a mitochondrial transporter sequence, wherein the hybrid nucleic acid sequence comprising the ATP 6 gene, when transformed into a recipient plant, causes male sterility; and wherein the nucleic acid sequence capable of transferring the said expressed protein to the mitochondrion is selected from the group consisting of:

the fragments encoding yeast tryptophanyl tRNA synthetase, the β sub-unit of *Nicotiana plumbaginifolia* ATPase, the maize ATP/ADP translocator, and a 303 base pair EcoRI/KpnI fragment comprising codons 1 to 62 of sub-unit IV of yeast cytochrome oxidase into the selected plants to form a transgenic plant of decreased male fertility;

(b) regenerating and culturing the transgenic plants obtained in (a); and (c) measuring the production and the viability of pollen from said transgenic plants.

16. Process for restoring male fertility to transgenic male-sterile plants, comprising the following steps:

(1) transforming a selected higher plant by introducing at least one copy of a hybrid nucleic sequence that is capable of modifying male fertility in plants having it incorporated therein, wherein said sequence comprises at least a coding region of an unedited mitochondrial gene from a higher plant, with which is associated a sequence capable of transferring the protein expressed by the said coding region to the mitochondrion, wherein:

the coding region of the unedited mitochondrial gene is the wheat ATP6 gene in unedited form and ligated to a mitochondrial transporter sequence, wherein the hybrid nucleic acid sequence comprising the ATP 6 gene, when transformed into a recipient plant, causes male sterility; and wherein the nucleic sequence capable of transferring the said expressed protein to the mitochondrion is selected from the group consisting of:

the fragments encoding yeast tryptophanyl tRNA synthetase, the β sub-unit of *Nicotiana plumbaginifolia* ATPase, the maize ATP/ADP translocator, and a 303 base pair EcoRI/KpnI fragment comprising codons 1 to 62 of sub-unit IV of yeast cytochrome oxidase into a recipient plant, by means of a plasmid containing said sequence, whereby obtaining a transgenic male-sterile plant;

(2) transforming the same higher plant as in (1), by introducing at least one copy of an antisense hybrid nucleic sequence comprising, in the reverse direction, at least the same coding region of the unedited plant mitochondrial gene as that contained in the said transgenic male-sterile plants obtained in (1), into a recipient plant, by means of a plasmid containing the said sequence, whereby obtaining transgenic male-fertile plants; and (3) crossing the transgenic male-sterile plants obtained in (1) and the male-fertile plants obtained in (2), in order to obtain hybrids.

* * * * *